US007367978B2

(12) United States Patent
Drewry et al.

(10) Patent No.: US 7,367,978 B2
(45) Date of Patent: *May 6, 2008

(54) ADJUSTABLE SPINAL TETHER

(75) Inventors: Troy D. Drewry, Memphis, TN (US); Michael C. Sherman, Memphis, TN (US); David L. Brumfield, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 174 days.

This patent is subject to a terminal disclaimer.

(21) Appl. No.: 10/224,305

(22) Filed: Aug. 20, 2002

(65) Prior Publication Data

US 2003/0023241 A1  Jan. 30, 2003

Related U.S. Application Data

(63) Continuation of application No. 09/421,976, filed on Oct. 20, 1999, now Pat. No. 6,436,099.

(60) Provisional application No. 60/130,910, filed on Apr. 23, 1999.

(51) Int. Cl.
*A61B 17/56* (2006.01)
(52) U.S. Cl. .......................................... 606/61; 606/74
(58) Field of Classification Search ................. 606/60, 606/61, 54, 53, 86, 74, 103; 24/16 R, 17 R, 24/18, 17 A, 17 B; 119/795
See application file for complete search history.

(56) References Cited

U.S. PATENT DOCUMENTS

| 788,136 A | 4/1905 | Heilrath |
| 2,561,487 A | 7/1951 | Bailhe |
| 3,693,616 A | 9/1972 | Roaf et al. |
| 4,041,939 A | 8/1977 | Hall |
| 4,078,559 A | 3/1978 | Nissinen |

(Continued)

FOREIGN PATENT DOCUMENTS

EP  0 478 470 A1  4/1992

(Continued)

OTHER PUBLICATIONS

*Spinal Surgery Before and After Paul Harrington*, Spine, Jun. 15, 1998, vol. 23, No. 12.

(Continued)

*Primary Examiner*—Eduardo C. Robert
*Assistant Examiner*—David Comstock
(74) *Attorney, Agent, or Firm*—Krieg DeVault LLP

(57) ABSTRACT

An improved apparatus is provided to allow for an adjustable length tether for use in the spine and other parts of the body. The tether comprises an artificial strand with an eyelet formed in one end, the other end being looped through the eyelet. The other end is then secured with respect to the eyelet by a crimp, the excess length being cut off after the length of the tether has been given an appropriate tension. Alternatively, the eyelet end may be formed around a grommet. The crimp may be separate from the grommet or a part of the grommet. The mechanism by which the length is adjusted in some cases will take advantage of the shape memory properties of alloys such as nickel-titanium.

17 Claims, 19 Drawing Sheets

U.S. PATENT DOCUMENTS

| | | |
|---|---|---|
| 4,570,618 A | 2/1986 | Wu |
| 4,573,454 A | 3/1986 | Hoffman |
| 4,686,970 A | 8/1987 | Dove et al. |
| 4,743,260 A | 5/1988 | Burton |
| 4,776,851 A | 10/1988 | Bruchman et al. |
| 4,870,957 A | 10/1989 | Goble et al. |
| 4,913,134 A | 4/1990 | Luque |
| 4,946,377 A | 8/1990 | Kovach |
| 4,955,910 A | 9/1990 | Bolesky |
| 4,966,600 A | 10/1990 | Songer et al. |
| 5,002,574 A | 3/1991 | May et al. |
| 5,011,484 A | 4/1991 | Breard |
| 5,019,093 A | 5/1991 | Kaplan et al. |
| 5,092,866 A | 3/1992 | Breard et al. |
| 5,092,868 A | 3/1992 | Mehdian |
| 5,116,340 A | 5/1992 | Songer et al. |
| 5,180,393 A | 1/1993 | Commarmond |
| 5,199,146 A | 4/1993 | Grover et al. |
| 5,306,301 A | 4/1994 | Graf et al. |
| 5,318,566 A | 6/1994 | Miller |
| 5,387,213 A | 2/1995 | Breard et al. |
| 5,395,374 A | 3/1995 | Miller et al. |
| 5,415,658 A | 5/1995 | Kilpela et al. |
| 5,415,661 A | 5/1995 | Holmes |
| 5,417,690 A | 5/1995 | Sennett et al. |
| 5,423,820 A | 6/1995 | Miller et al. |
| 5,425,767 A | 6/1995 | Steininger et al. |
| 5,456,722 A | 10/1995 | McLeod et al. |
| 5,476,465 A | 12/1995 | Preissman |
| 5,496,318 A | 3/1996 | Howland et al. |
| 5,536,270 A | 7/1996 | Songer et al. |
| 5,540,698 A | 7/1996 | Preissman |
| 5,540,703 A | 7/1996 | Barker, Jr. et al. |
| 5,545,168 A | 8/1996 | Burke |
| 5,569,253 A | 10/1996 | Farris et al. |
| 5,607,425 A | 3/1997 | Rogozinski |
| 5,609,634 A | 3/1997 | Voydeville |
| 5,628,756 A | 5/1997 | Barker, Jr. et al. |
| 5,649,927 A | 7/1997 | Kilpela et al. |
| 5,653,711 A | 8/1997 | Hayano et al. |
| 5,669,917 A | 9/1997 | Sauer et al. |
| 5,693,046 A | 12/1997 | Songer et al. |
| 5,702,395 A | 12/1997 | Hopf |
| 5,702,399 A | 12/1997 | Kilpela et al. |
| 5,707,395 A | 1/1998 | Li |
| 5,720,747 A | 2/1998 | Burke |
| 5,725,582 A | 3/1998 | Bevan et al. |
| 5,741,260 A | 4/1998 | Songer et al. |
| 5,772,663 A | 6/1998 | Whiteside et al. |
| 5,908,421 A | 6/1999 | Beger |
| 5,964,765 A | 10/1999 | Fenton, Jr. et al. |
| 5,993,452 A | 11/1999 | Vandewalle |
| 6,086,590 A | 7/2000 | Margulies et al. |
| 6,296,643 B1 | 10/2001 | Hopf et al. |

FOREIGN PATENT DOCUMENTS

| | | |
|---|---|---|
| EP | 0 625 336 A2 | 11/1994 |
| FR | 2 704 745 | 10/1994 |
| GB | 2 269 753 A | 2/1994 |
| GB | 2 276 823 A | 10/1994 |
| JP | 63-95060 | 9/1986 |
| SU | 839515 | 6/1981 |
| WO | WO 94/26192 | 11/1994 |
| WO | WO 95/22294 | 8/1995 |
| WO | WO 95/26165 | 10/1995 |
| WO | WO 96/17544 | 6/1996 |
| WO | WO 99/09891 | 3/1999 |

OTHER PUBLICATIONS

*Atlas of Spinal Operations*, Bauer, Kerschbaumer and Poisel, Thieme Medical Publishers, Inc., 1993.

*The Use of Sublaminar Cables to Replace Luque Wires*, Songer, Spencer, Meyer and Jayaraman, Spine, vol. 16, No. 85, Aug. 1991 Supplement.

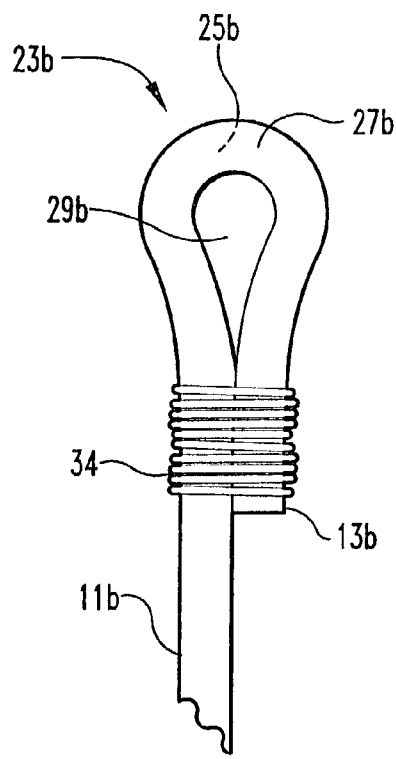
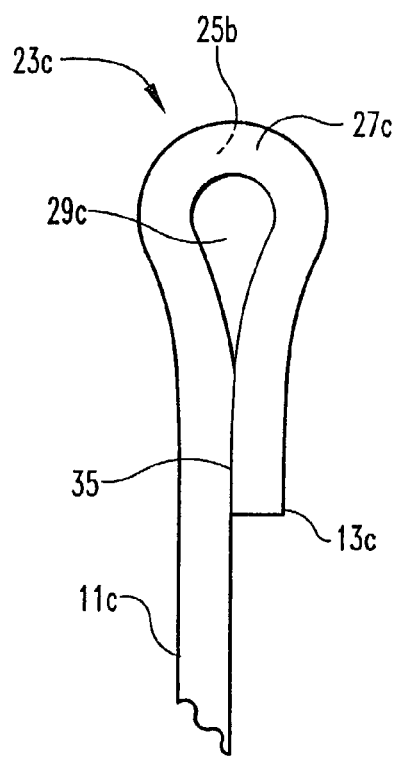
Fig. 3    Fig. 4
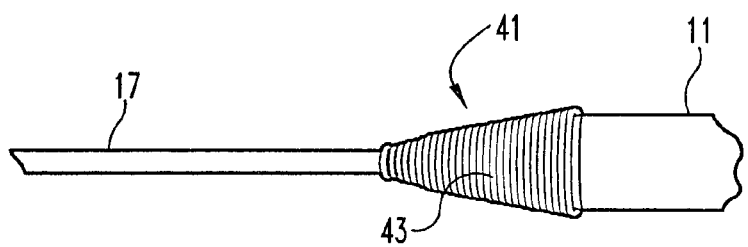
Fig. 6
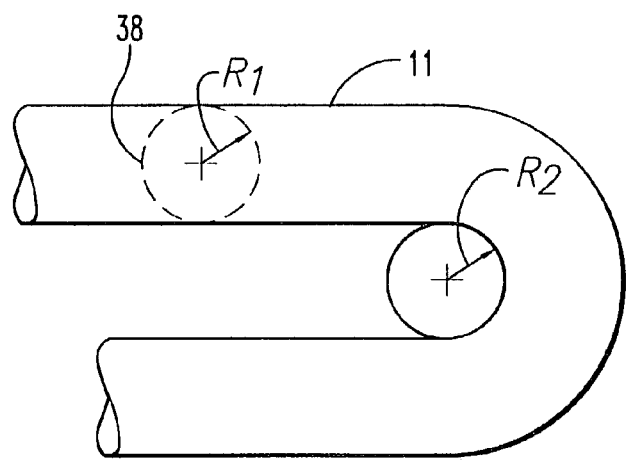
Fig. 5

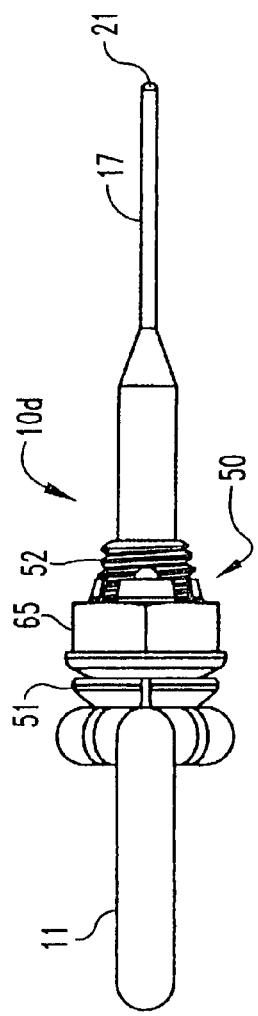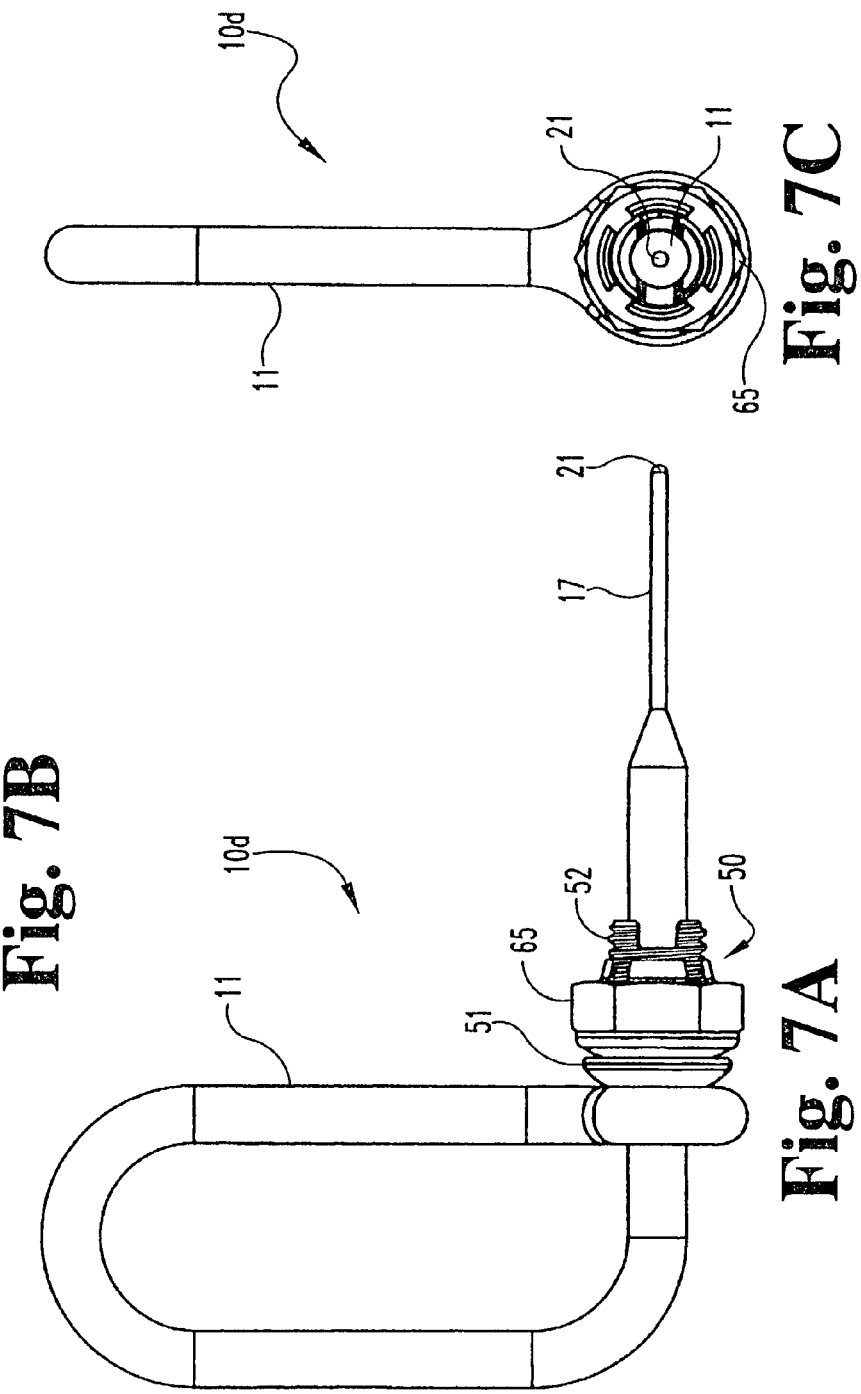

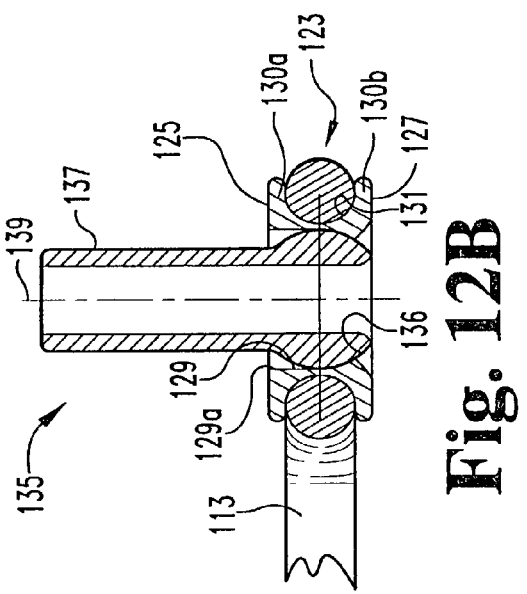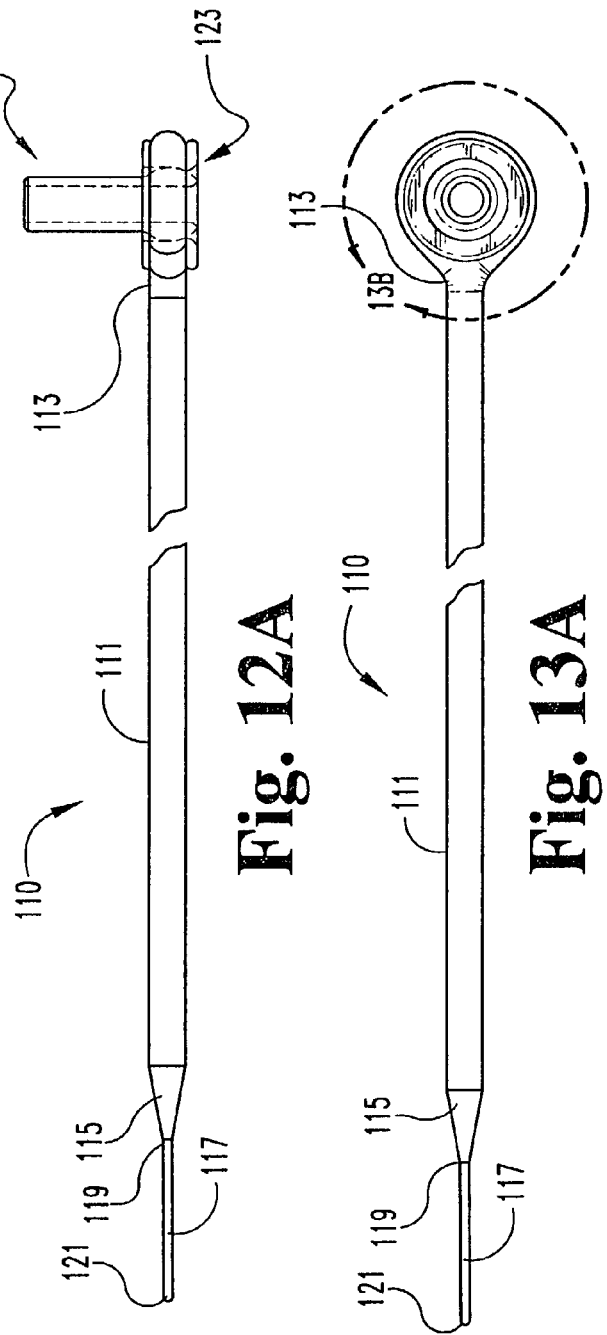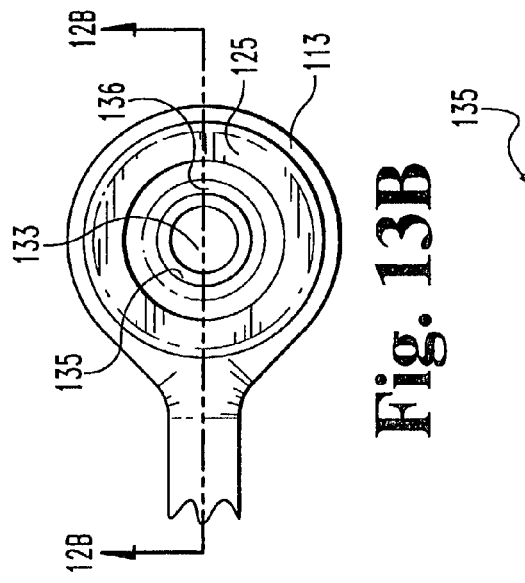

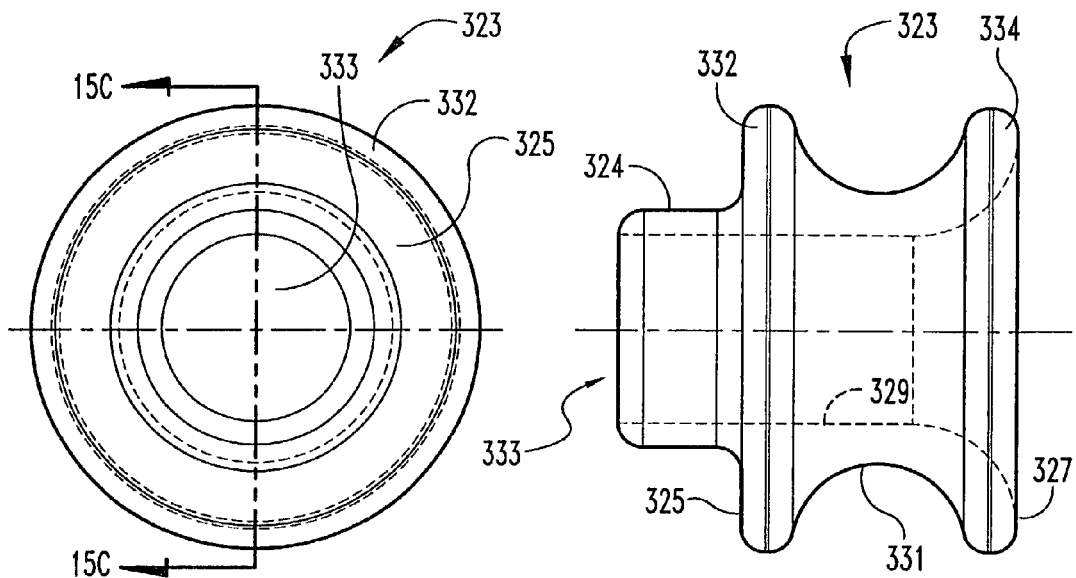
Fig. 15A  Fig. 15B
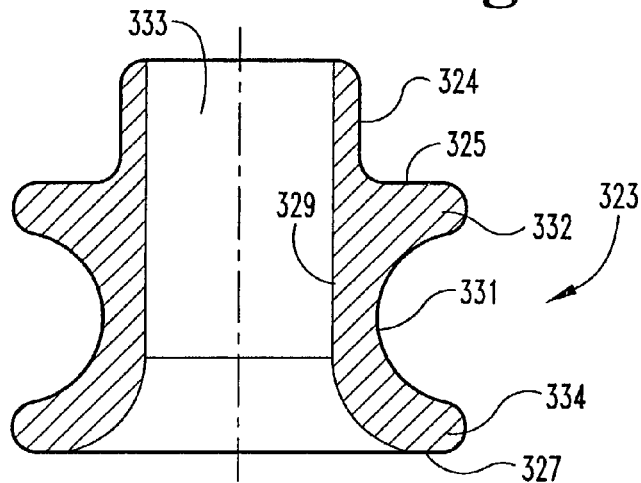
Fig. 15C
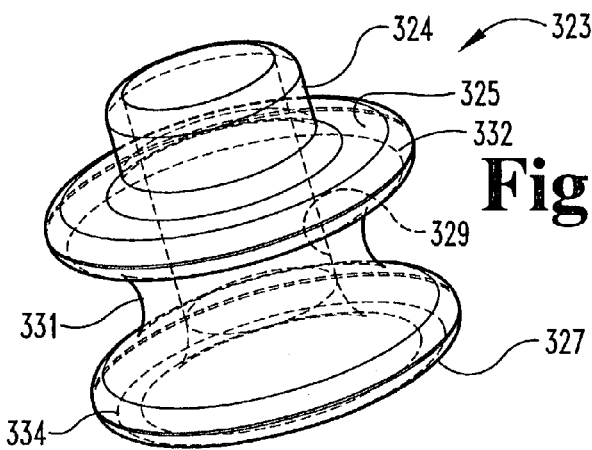
Fig. 15D

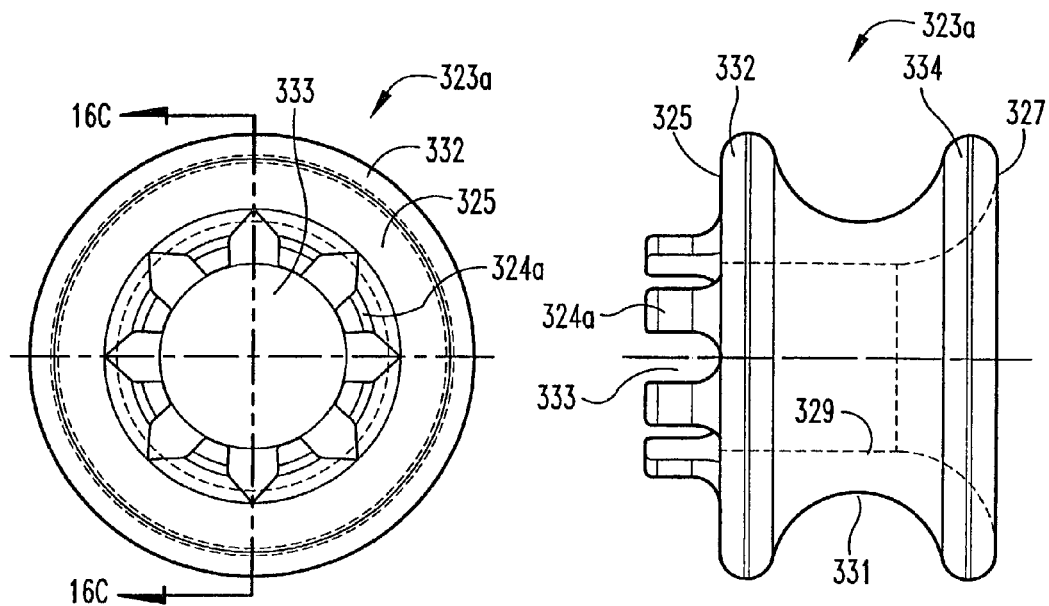
Fig. 16A  Fig. 16B
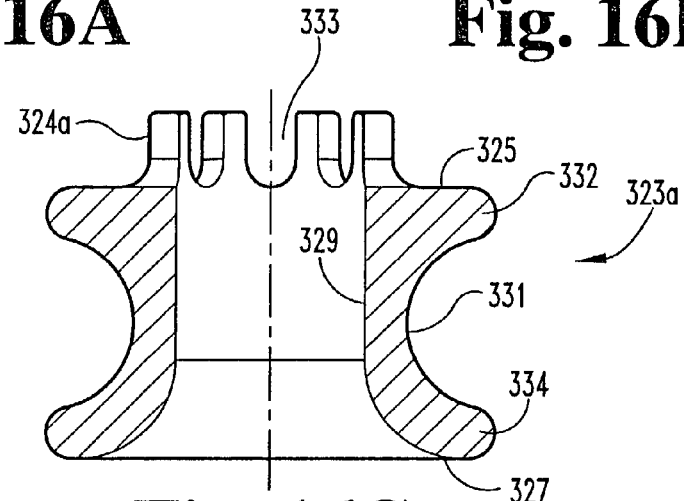
Fig. 16C
Fig. 16D

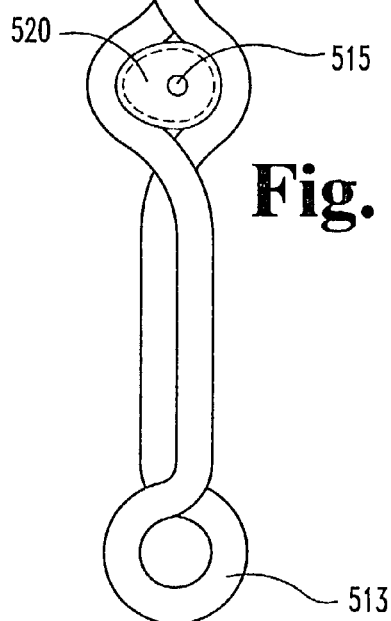
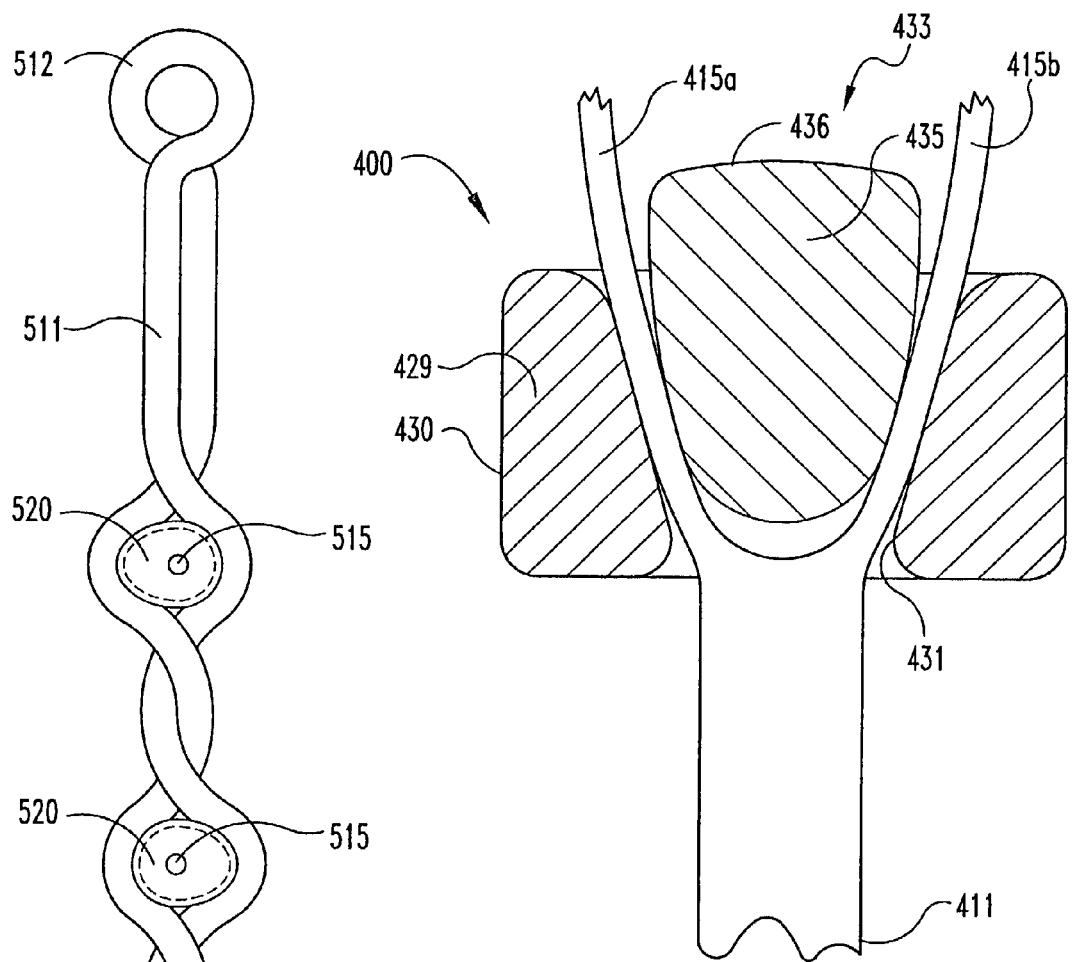
Fig. 19
Fig. 20A
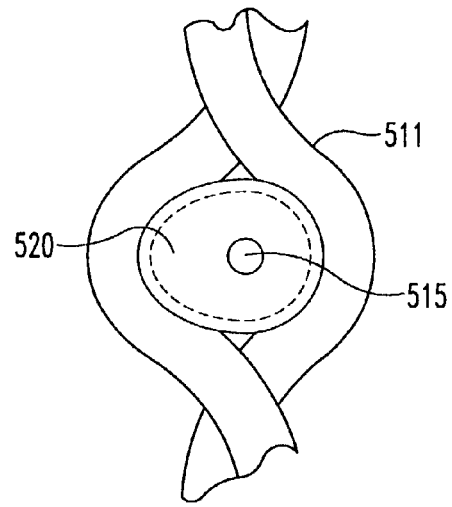
Fig. 20B

ADJUSTABLE SPINAL TETHER

CROSS REFERENCE TO RELATED APPLICATIONS

The present application is a continuation of U.S. patent application Ser. No. 09/421,976, filed on Oct. 20, 1999, now U.S. Pat. No. 6,436,099 B1, which claims the benefit of Provisional Application Ser. No. 60/130,910, filed on Apr. 23, 1999, the contents of each application hereby being incorporated by reference.

BACKGROUND OF THE INVENTION

Various types of spinal column disorders are known and include scoliosis (abnormal curvature of the spine), kyphosis (backward curvature of the spine), spondylolisthesis (forward displacement of a lumbar vertebra), and other disorders such as ruptured or slipped discs, broken or fractured vertebrae, and the like. Procedures to stabilize areas of the spine for both fusing spinal vertebrae together and for other stabilization purposes often require the use of a spinal tether. The existing spinal tethers, of which we are aware on the market, come in straight lengths or circular, "loop" geometries. These tethers typically rely on implants, anchors, or knots to secure the tether to the spine. Additionally, such implants are of fixed length requiring careful measurement of the distance around the anatomy to which the tether is secured or between the anchor points to which the tether is attached. Such precise measurement is difficult prior to surgery and, when done during surgery, results in longer operating times as measurements are taken and a spinal tether of the appropriate length is manufactured.

SUMMARY OF THE INVENTION

In one embodiment, the apparatus comprises an adjustable tether having a polymer strand with a first end and a second end and a first end portion and second end portion between the first end and the second end. The polymer strand has an intermediate portion between the end portions. The first end is secured in wrapped condition to form an eyelet in the first end portion. The eyelet has a first side and a second side and an aperture defined between the first side and the second side. The aperture has a cross-section such that the second end may pass therethrough in the direction from one of the sides to the other of the sides. The apparatus further includes a crimp with a bore defined therethrough. The intermediate portion of the tether extends through the bore. The crimp has a first portion with a cross-section such that the first portion will not pass through the aperture. The crimp has a first state and a second state, the first state permitting the polymer strand to move within the bore, the second state locking the intermediate portion within the bore wherein the intermediate portion is received in the bore only once.

In another embodiment, the apparatus comprises an adjustable tether having a polymer strand with a first part and a second part, each of the parts between a first end portion and a second end portion. The first part is closer to the first end portion than the second part. The first end portion is wrapped around and contacts the first part to form an eyelet with a first side and a second side. The apparatus has attachment means for holding the first end portion in contact with the first part. The eyelet has an aperture defined between the first side and the second side, the aperture having a cross-section such that the second end may pass therethrough. The second end portion passes through the aperture in the direction from the first side to the second side to form a loop with a length and the apparatus has means for fixing the length of the loop.

In another embodiment, the apparatus comprises a grommet with a top surface and a bottom surface and interior and exterior side surfaces extending between the top surface and the bottom surface. The interior side surface defines an aperture between the top surface and the bottom surface. The apparatus also includes an artificial strand having a first end portion and a second end portion. The first end portion is attached to the grommet and the second end portion passes through the aperture in a direction from the bottom surface to the top surface to form a loop. The apparatus further includes a crimp with a bore defined therethrough, the second end portion passing through the bore. The crimp has a first portion with a cross-section such that the first portion of the crimp will not pass through the aperture. The crimp has a first state and a second state. The first state permits the artificial strand to move within the bore, the second state locks a portion of the artificial strand within the bore.

In yet another embodiment the apparatus comprises a grommet with a top surface and a bottom surface and interior and exterior side surfaces extending between the top surface and the bottom surface. The interior side surface defines an aperture between the top surface and the bottom surface. The apparatus also includes an artificial strand with a first end portion and a second end portion and means for attaching the first end portion to the grommet. The second end portion passes through the aperture in a direction from the bottom surface to the top surface to form a loop.

BRIEF DESCRIPTION OF THE DRAWINGS

FIG. 3 is an enlarged partial view of an embodiment of the adjustable tether in which one end is wrapped around and sewn with a thread.

FIG. 4 is a close up of one end portion of the adjustable tether which is wrapped around and joined along a contact surface.

FIG. 5 is illustrative of the flexibility of one embodiment of the artificial strand of the adjustable tether.

FIG. 6 is an enlarged view of the interconnection between a leader and an artificial strand.

FIGS. 7A-D are side, side, top, and perspective views respectively of another embodiment of the adjustable tether.

FIG. 12A is a side elevational view of an adjustable tether with a grommet at one end having a socket receiving a ball portion of a crimp.

FIG. 12B is an enlarged cross-sectional view of the ball and socket crimp-grommet of FIG. 12A.

FIG. 13A is a top plan view of the adjustable tether of the FIG. 12A.

FIG. 13B is an enlarged view of the grommet and crimp end of the adjustable tether of FIG. 13A.

FIG. 15A is a top plan view of an embodiment of a crimping grommet.

FIG. 15B is a side view of the embodiment of the crimping grommet of FIG. 15A.

FIG. 15C is a cross-sectional view along the lines A-A of the crimping grommet of FIG. 15A.

FIG. 15D is a perspective view of the crimping grommet of FIG. 15A.

FIG. 16A is a top plan view of another embodiment of a crimping grommet.

FIG. 16B is a side view of another embodiment of the crimping grommet of FIG. 16A.

FIG. 16C is a cross-sectional view along the direction A-A of the crimping grommet of FIG. 16A.

FIG. 16D is a perspective view of the crimping grommet of FIG. 16A.

FIG. 19 is an enlarged partial view of another embodiment of the adjustable tether having a plug and ring design.

FIGS. 20A and 20B are top views of oval shaped cams interacting with an artificial strand to tension the artificial strand.

DESCRIPTION OF THE PREFERRED EMBODIMENT

Figure 1A:
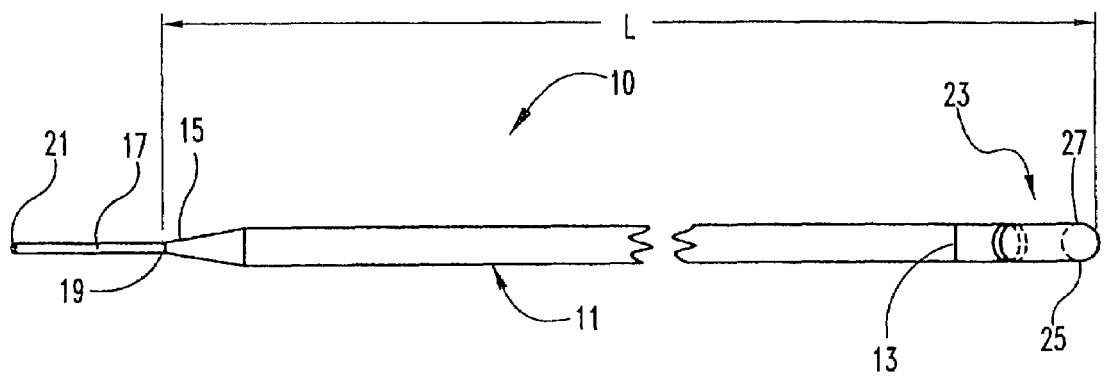
FIG. 1A is a side elevational view of the adjustable tether of an embodiment of the adjustable tether of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

Figure 1B:
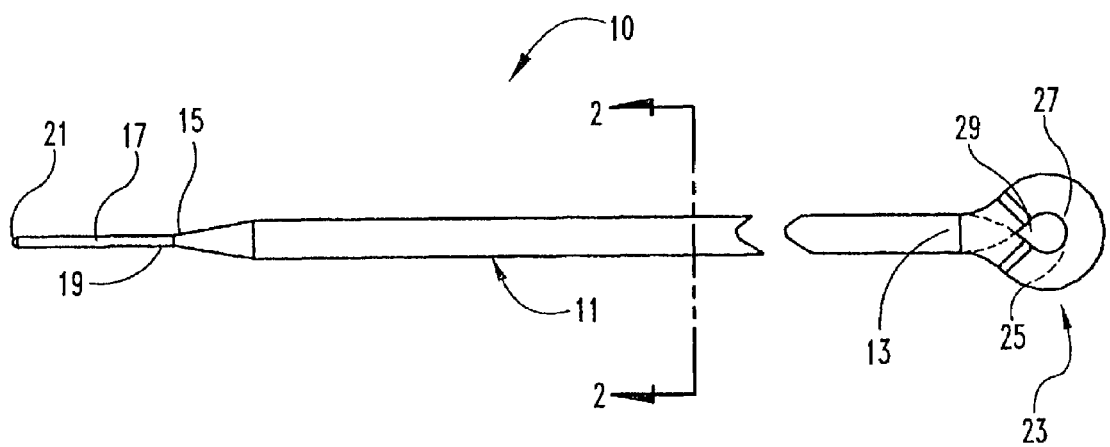
FIG. 1B is a top view of the embodiment of FIG. 1A.

With reference to FIGS. 1A and 1B, an adjustable spinal tether 10 comprises a leader 17 attached to an artificial strand 11. Artificial strand 11 has a first end 13 and a second end 15. The total length L of strand portion of the tether is preferably about one meter. This length may be varied as desired. Leader 17 has a first end 19 which is attached to the second end 15 of artificial strand 11. The second end of leader 17 has a tip 21. Tip 21 may be blunt or sharp as desired. The first end portion 13 of artificial strand 11 is wrapped around and attached to artificial strand 11 to form an eyelet 23 with a first side 25 and a second side 27 with an aperture 29 defined in the eyelet. The adjustable spinal tether 10 will also include a crimp (not shown), various embodiments of which will be discussed further below.

Figure 2:
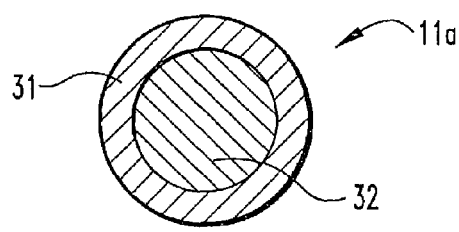
FIG. 2 is a cross-sectional view of the strand of the embodiment of FIG. 1B along the lines 2-2.

With reference to FIG. 2, the cross-section of one preferred embodiment of the artificial strand 11a is a coaxial design with an outer sheath 31 and an inner core 32. The inner core 32 and outer sheath 31 are both preferably made of a braided polymer such as polyester, polypropylene, or polyethylene. The inner core 32 and outer sheath 31 may be made of different polymers. In one embodiment the inner core 32 and outer sheath 31 are both made of polyethylene. In another embodiment the inner core 32 is braided for strength. In yet another embodiment, the outer sheath 31 is braided for abrasion resistance. The outer sheath is braided for abrasion resistance by weaving it in such a manner that the outer sheath 31 is unloaded and has no tensile force applied to it. In a preferred embodiment, the inner core 32 and outer sheath 31 are both made of polyethylene with the inner core 32 being braided for strength and the outer sheath 31 being braided for abrasion resistance. It should be understood that other designs such as multi-layered designs with a plurality of successive outer sheaths or a monofilament or single fiber design are within the scope of the invention. It should be further understood that artificial strand 11 may be manufactured from a variety of materials, including, but not limited to, conventional biocompatible implant alloys such as titanium, stainless steel, cobalt-chrome alloys, or even shape memory alloys and materials such as nickel-titanium.

With reference to FIG. 3, one embodiment of artificial strand 11b has a first end portion 13b which is wrapped back around on artificial strand 11b to form an eyelet 23b with a first side 25b and a second side 27b defining an aperture 29b in the eyelet. In this embodiment the first end portion 13b is sewn by threading 34 to attach it to artificial strand 11b. With reference to FIG. 4, in another embodiment artificial strand 11c has a first end portion 13c wrapped back around itself to form an eyelet 23c with an aperture 29c having a first side 25c and a second side 27c. In the embodiment in FIG. 4 the first end portion 13c contacts the artificial strand 11c along a line or surface 35. The first end portion 13c may be attached or coupled along contact portion 35 to the artificial strand 11c in a variety of manners. For example, a crimp (not shown) encircling part or all of both strand 11c and first end portion 13c may hold the loop/eyelet formation. Alternatively, an adhesive could be applied on first end portion 13c and strand 11c at contact portion 35 to hold first end 13c in a loop configuration with eyelet 23c. In other possible embodiments first end portion 13c could be swaged, press fit, or even welded against 11c if strand 11 is a metal, to secure it. In yet another embodiment the strand 11c is a polymer as is first end portion 13c, both of which may be ultrasonically or otherwise melted along contact surface or line 35 and then allowed to resolidify while in contact to fuse first end portion 13c to artificial strand 11c.

In one embodiment the adjustable spinal tether is constructed of a braided polymer with the previously described coaxial design in which the inner core 32 and outer sheath 31 are both made of polyethylene and the inner core 32 is braided for strength while the outer sheath 31 is braided for abrasion resistance. In one preferred embodiment, the polyethylene and braiding pattern selected are such that the adjustable tether 10 has a minimum strength of 500 kg, a diameter less than 4 mm, low elongation, a circular cross-section, and is able to bend around a radius equal to the radius of the tether. For example, with reference to FIG. 5, artificial strand 11 has a circular cross-section 38 with a radius $R_1$ and has a flexibility sufficient to bend around a radius $R_2$ where the radius $R_2$ is equal to the radius $R_1$. It should be understood that artificial strand 11 may be manufactured to have a variety of strength and elongation requirements depending on the application. It should be further understood that artificial strand 11 may be made of materials which have cross-sections other than circular, including, but not limited to, oval or elliptical, square, triangular, polygonal and others as known to those of ordinary skill in the art.

With reference to FIG. 6, leader 17 may be attached to artificial strand 11 in a variety of manners. In the embodiment shown in FIG. 6 the interconnection 41 between leader 17 and artificial strand 11 is secured by thread 43 sewing leader 17 onto artificial strand 11. In other embodiments the leader 17 may be swaged, press fit, or even welded (in cases where both the leader 17 and artificial strand 11 are metal) onto artificial strand 11. In one embodiment the leader 17 is made of soft, malleable commercially pure titanium (ASTM F67-95). In another embodiment the leader 17 is made out of a polymer. In one embodiment where leader 17 is made out of a polymer and artificial strand 11 is made of a polymer, the leader 17 may be integrally formed with artificial strand 11 by being extruded with strand 11, leader 17 preferably having a smaller cross-section for facilitating insertion through either various portions of the anatomy and/or through the aperture 29 defined in eyelet 23 formed at first end 13 of adjustable spinal tether 10.

Figure 7D:
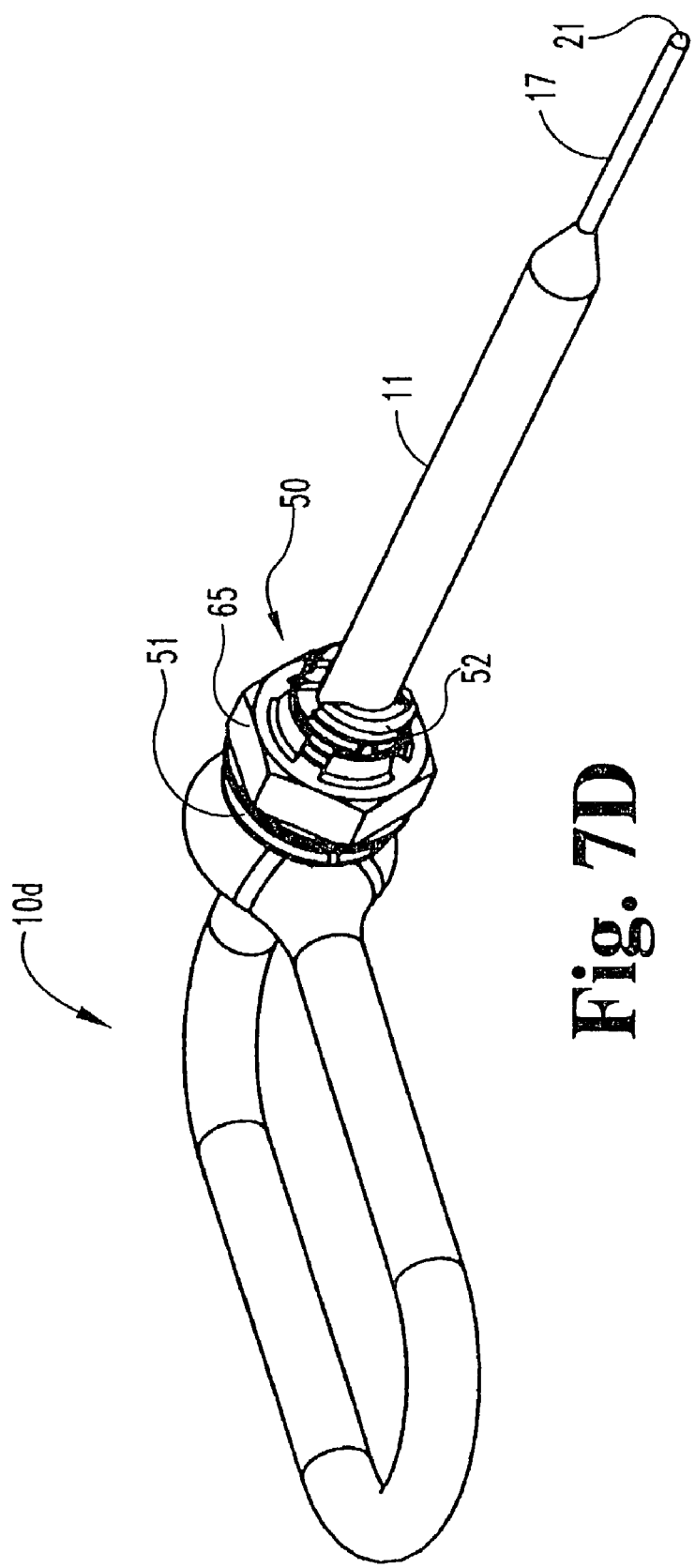
Figure 8:
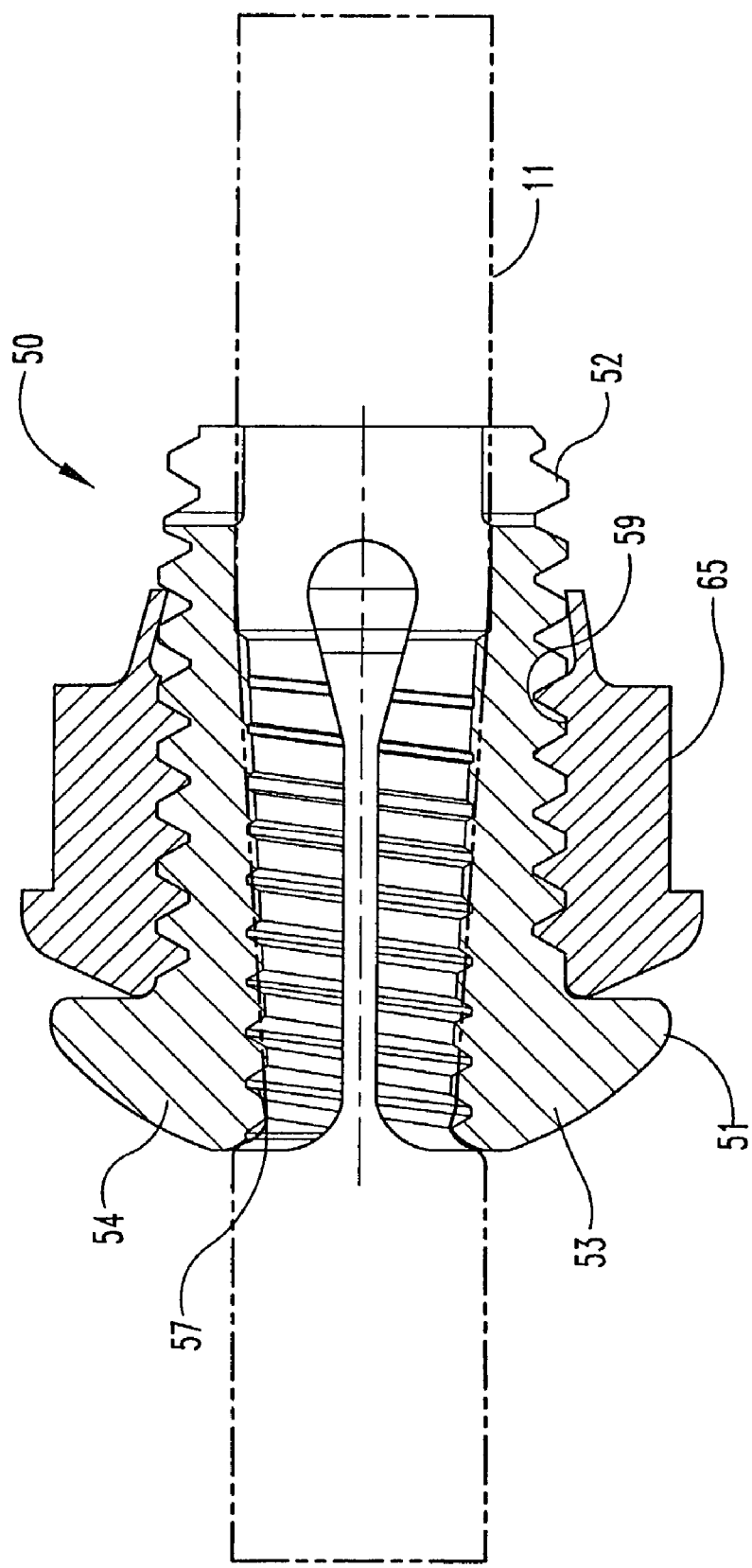
FIG. 8 is an enlarged cross-sectional view of the crimp and locknut of the embodiment of FIG. 7.
Figure 9A:
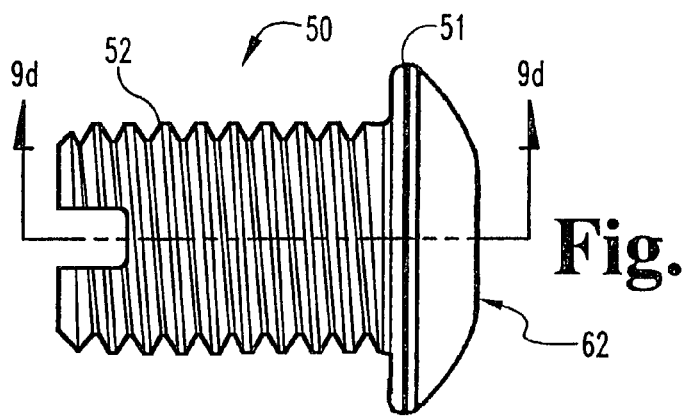
FIG. 9A is a side elevational view of the crimp of FIG. 7.
Figure 9B:
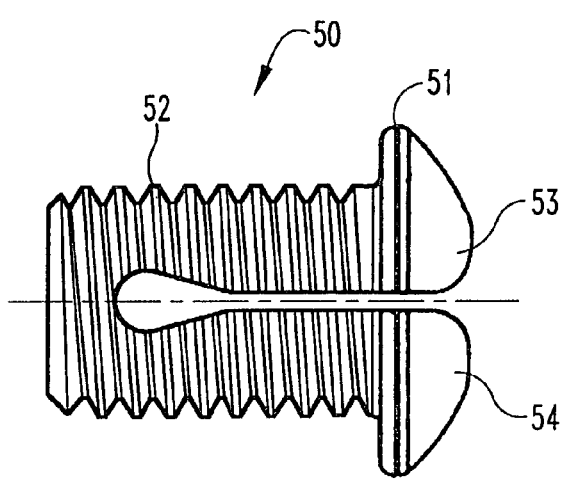
FIG. 9B is another side elevational view of the adjustable tether of FIG. 7.
Figure 9C:
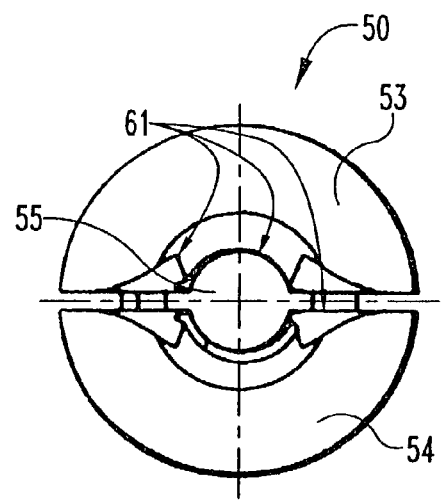
FIG. 9C is a bottom plan view of the crimp of FIG. 7.
Figure 9D:
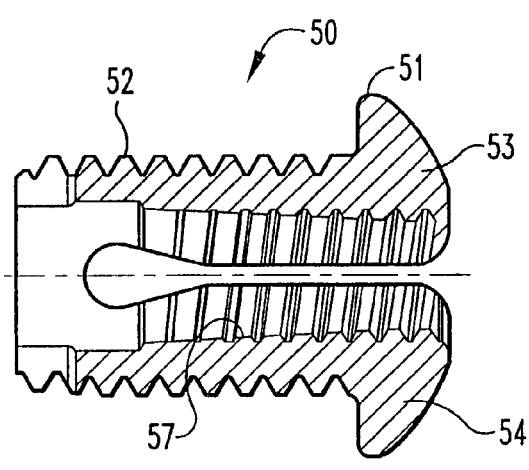
FIG. 9D is a cross-sectional view of the crimp of FIG. 7 along the direction 9d in FIG. 9A.
Figure 9E:
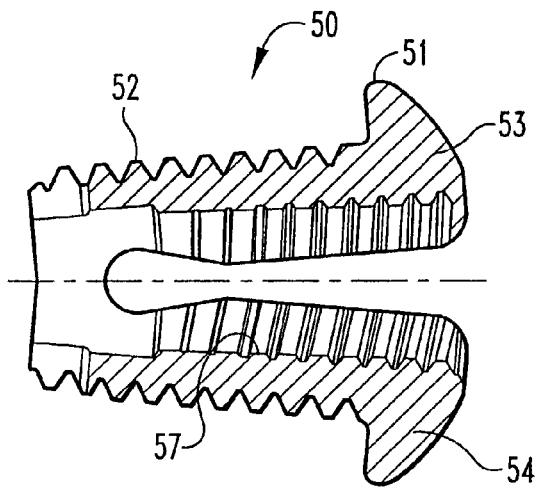
FIG. 9E is a cross-sectional view of FIG. 9A along the direction 9d when the crimp is in its deformable first state to more easily allow the artificial strand to extend through the bore in the mechanical crimp.

FIGS. 7-9 show an embodiment of the adjustable spinal tether 10d (with like elements labeled as previously) having a mechanical crimp 50 with a castellated locknut 65 (locknut 65 is available from the assignee of the present application as Part No. 843-160). Artificial strand 11 has an opening formed at first end 13 which may or may not include a grommet as discussed further below. The second end of artificial strand 11 has a leader 17 with a tip 21 which is threaded through the opening formed at the first end of artificial strand 11. Additionally, leader 17 at the second end of artificial strand 11 is threaded through a bore 55 (FIG. 9C) defined by interior surface 57 (FIG. 9D) of mechanical crimp 50.

Mechanical crimp 50 has a first portion 51 with a cross-section which is preferably larger than the cross-section of opening or eyelet defined at the first end of artificial strand 11. The cross-section of first portion 51 does not have to be larger than that of the eyelet formed in strand 11 so long as the shape of first portion 51 is such that it cannot pass through the aperture defined in the eyelet. Crimp 50 preferably has a generally circular cross-section. Interior surface 57 of crimp 50 preferably has grooves. It should be understood that crimp 50 may have a variety of cross-sections. It should be further understood that the cross-section of interior surface 57 defining bore 55 may vary along the longitudinal axis of bore 55. The outer surface of crimp 50 has external threading 52 defined thereon. External threading 52 is compatible with the internal threading 59 of locknut 65.

The mechanical crimp 50 has a first branch 53 and a second branch 54 which are in a deformable first state (see FIG. 9E) when mechanical locknut 65 is not threaded upon external threading 52. When mechanical crimp 50 is in the first state, leader 17 and artificial strand 11 may pass through bore 55. In the second state mechanical crimp 50 has locknut 65 threaded on external threading 52 compressing first branch 53 and second branch 54 together onto artificial strand 11 and thus minimizing or preventing movement of artificial strand 11 with respect to mechanical crimp 50. The cross-section and internal grooves or threading of interior surface 57 defining bore 55 preferably narrows along the longitudinal axis of crimp 50 as shown best in FIG. 8 to firmly grasp artificial strand 11. First portion 51 preferably has its largest cross-section in a direction perpendicular to the longitudinal axis of bore 55 so that first portion 51 of crimp 50 is prevented from passing through the opening defined on the first end of artificial strand 11. It should be understood, however, that first branch 53 and second branch 54 may have a variety of shapes some of which will not fit within the aperture. First branch 53 and second branch 54 of crimp 50 are preferably shaped so as to be partially received within the aperture of the eyelet (or grommet if present) defined on first end 13 of artificial strand 11. With reference to FIGS. 9A-9D further detail of mechanical crimp 50 is shown. It should be understood (see FIG. 9C) that in some embodiments glass beads 61 are preferably placed all over the bottom 62 of crimp 50. It should be further understood that crimp 50 preferably has no sharp edges on its bottom 62.

Figure 10A:
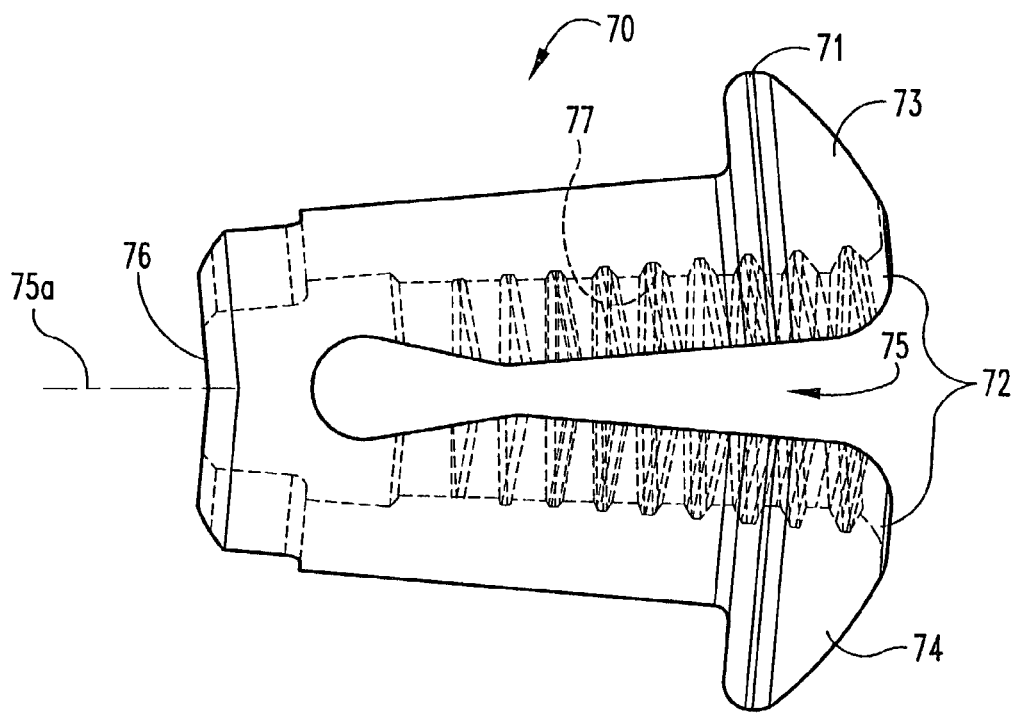
FIGS. 10A and 10B are side views with sectional view drawn in phantom lines of a shape memory crimp for use with an embodiment of the adjustable tether.
Figure 10B:
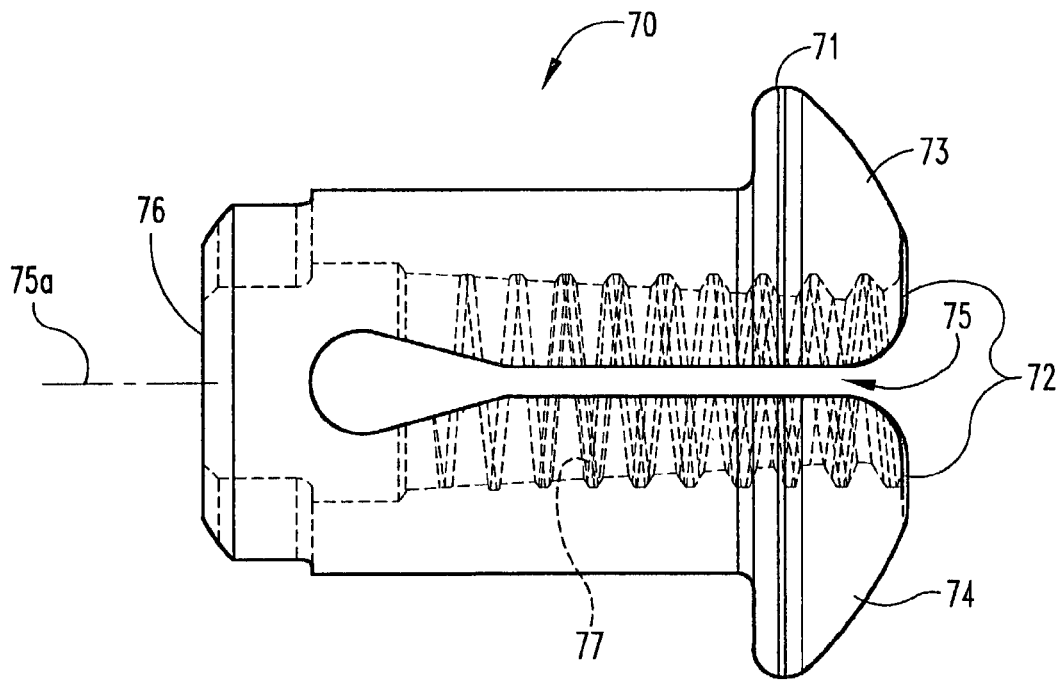

With reference to FIGS. 10A and 10B, another embodiment for the crimp of the adjustable spinal tether 10 is the shape memory alloy ("SMA") crimp 70. SMA crimp 70 has a first portion 71 which preferably defines the largest cross-section of crimp 70. It should be understood that either: (a) the cross-section of first portion 71 is larger than the cross-section of the aperture of the eyelet (or grommet if present as discussed further below) on the first end 13 of artificial strand 11, or (b) the cross-section of first portion while smaller in total area has a shape such that it may not pass through the aperture of the eyelet (or grommet). SMA crimp 70 has a first branch 73 and a second branch 74 interconnected by a top portion 76. SMA crimp 70 has an inner surface 77 which preferably has grooves therein. Inner surface 77 defines a bore 75 extending from the top 76 to the bottom 72 of SMA crimp 70. In one preferred embodiment the bore 75 narrows in width when progressing from top 76 to bottom 72. It should be understood that, if desired, the general shape and configuration of SMA crimp 70 may be similar to that of mechanical crimp 50 as shown in FIGS. 9A-9D.

With reference to FIG. 10A the SMA crimp 70 is shown in its first or martensitic state where it may be malleable or deformable. It should be understood that SMA crimp 70 in FIG. 10A may be in an austenitic state but at a temperature such that it may be deformed as shown under the influence of stress causing the formation of stress induced martensite which will reform to the initial memorized austenitic or second state upon the release of the stress. In the second or austenitic state the SMA crimp 70 has the shape shown in FIG. 10B with first branch 73 and second branch 74 closer together.

In either case, whether initially martensitic which is heated or stress induced martensitic which reforms to austenitic upon the release of stress, the second state of the crimp as shown in FIG. 10B has first branch 73 and second branch 74 closer together in a direction transverse to the longitudinal axis 75a of bore 75 extending between top 76 and bottom 72. The reformation to the memorized shape of SMA crimp 70 as shown in FIG. 10B causes inner surface 77 to be compressed onto artificial strand 11 and prevents or minimizes motion of artificial strand 11 relative to SMA crimp 70. It should be understood that SMA crimp 71 may have a second state in which crimp 70 has some portion remaining in the stress-induced martensitic phase while still providing compression sufficient to prevent or minimize motion of artificial strand 11 relative to SMA crimp 70.

Figure 11A:
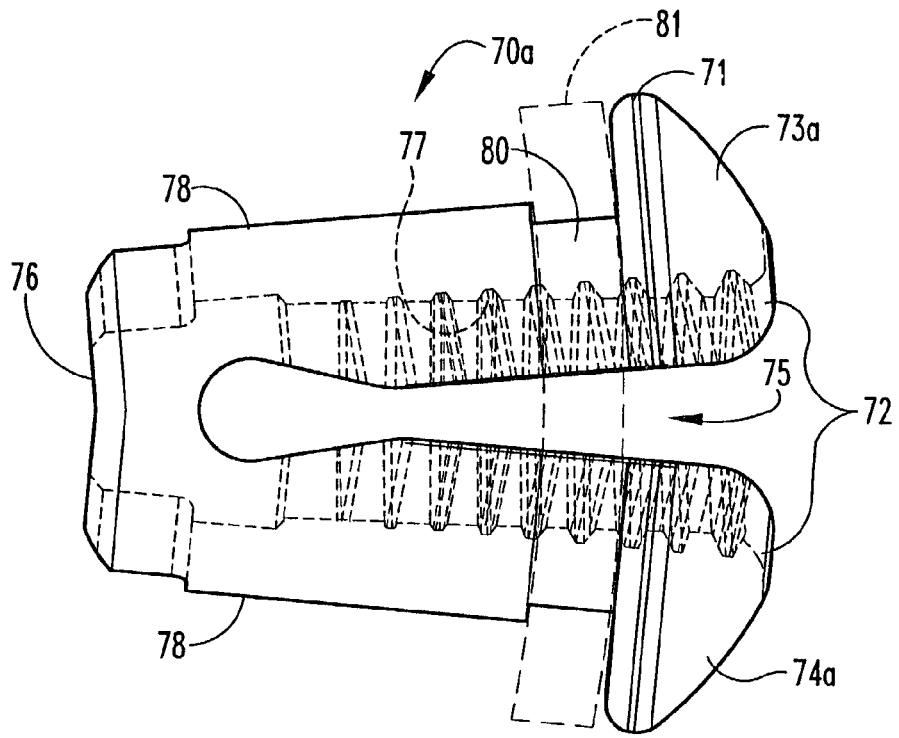
FIGS. 11A-C are side views with sectional view drawn in phantom lines of another embodiment of the crimp using shape memory technology.
Figure 11B:
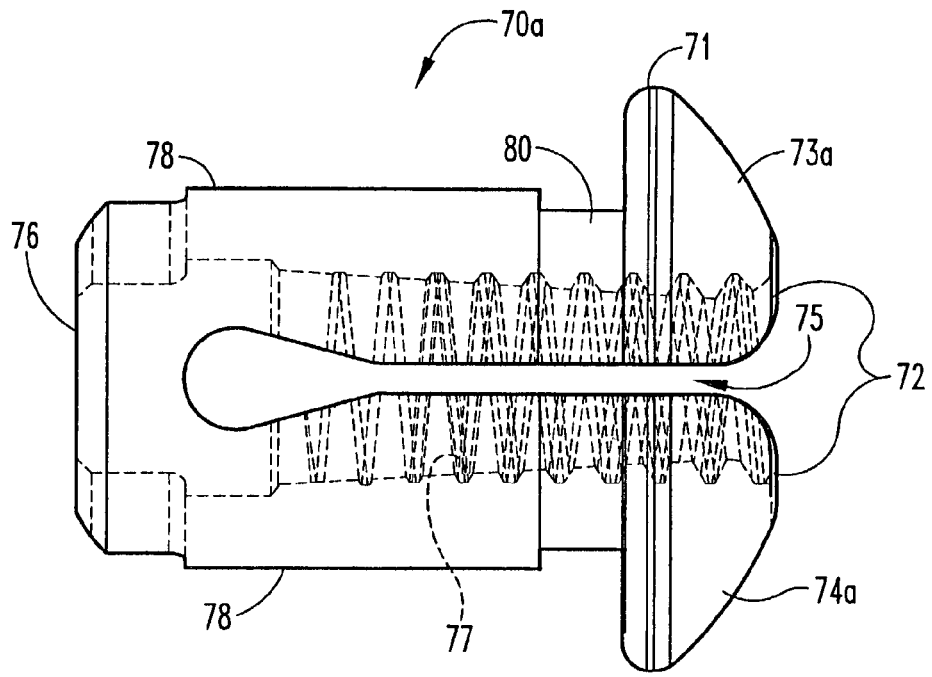
Figure 11C:
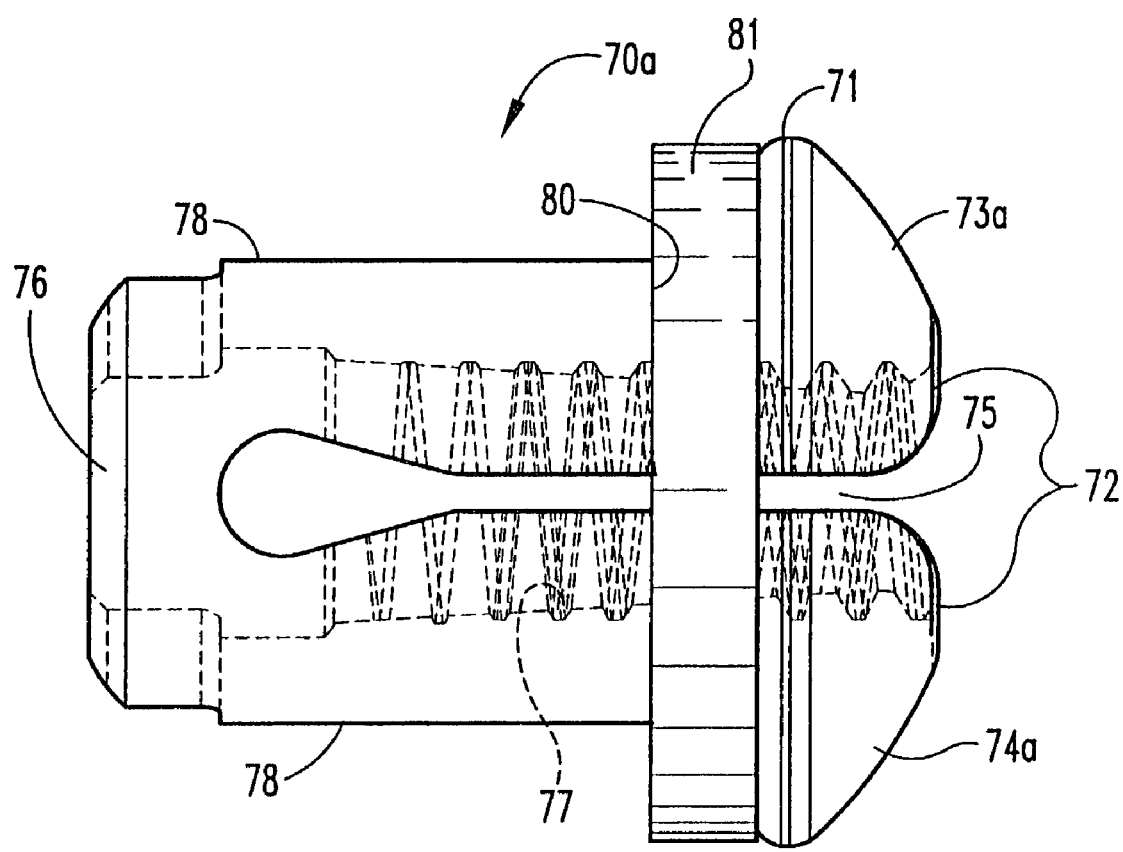

With reference to FIGS. 11A-11C, an alternative embodiment using the property of shape memory alloys to create a tether crimp 70a is illustrated. Like elements are labeled as previously. The tether crimp 70a has a first branch 73a and a second branch 74a which preferably define a groove 80 on the outer surface 78. The groove 80 is sized to receive a shape memory alloy compression element 81. In this embodiment, instead of constructing the crimp 70a itself or portions thereof of shape memory alloy as in SMA crimp 70, the crimp 70a is made of some malleable or deformable material which is partially or totally surrounded by SMA compression element 81 shown in its martensititc phase by the dotted line 81m in FIG. 11A.

In FIG. 11C the SMA compression element 81 is in the austenitic phase. When compression element 81 is in the martensitic phase, whether temperature or stress induced, the deformed shape (see FIG. 11A) of crimp 70a is such that the bore 75 is open to allow artificial strand 11 to be inserted therethrough. In the second state (FIG. 11C), the SMA compression element 81 attempts to return to its original or memorized shape which closes the first branch 73a and second branch 74a of tether crimp 70a around artificial strand 11. This prevents or minimizes motion of artificial strand 11 with respect to crimp 70a.

It should be understood that groove 80 on the outer surface 78 and grooves on the interior surface 77 defining bore 75 may be added or removed as desired and are not necessary for securing artificial strand 11 within SMA crimp 70 or within the combination of tether crimp 70a and compression element 81. It should be further understood that other embodiments in which a combination of a tether crimp made in whole or in part of a SMA as well as a SMA compression element is contemplated as within the scope of the invention. It should also be understood that SMA compression element may take a variety of shapes and cross-sections including, but not limited to, a circular ring, oval, elliptical, square, triangular, or other polygons, exterior or interior. SMA compression element may be sized to contact outer surface 78 and/or groove 80 all the way around the exterior or at just a few points. Similarly, it should be understood that groove or track 80 may take a variety of shapes including, but not limited to, the same rounded or polygonal structure as SMA compression element 81 to prevent slip between element 81 and groove 80.

With reference to FIGS. 22A-22D, another embodiment of a SMA tether crimp 170 is illustrated. SMA crimp 170 has a first portion 171 which preferably defines the largest cross-section of crimp 170. It should be understood that either: (a) the cross-section of first portion 171 is larger than the cross-section of the aperture of the eyelet (or grommet if present as discussed further below) on the first end 13 of artificial strand 11, or (b) the cross-section of first portion while smaller in total area has a shape such that it may not pass through the aperture of the eyelet (or grommet). SMA crimp 170 has a first branch 173 and a second branch 174 interconnected by a bottom portion 172. SMA crimp 170 has an inner surface 177 defining a bore 175 extending along centerline 175a from the top 176 to the bottom 172 of SMA crimp 170. In one embodiment the bore 175 narrows in width when progressing from bottom 172 to top 176. It should be noted that one advantageous feature of the SMA crimp 170 in FIGS. 22A-22D is the undulations 178 defined in branches 173 and 174. It should be understood that such undulations will reduce the possibility of axial slip. The increased surface area at the interface between SMA crimp 170 and an artificial strand will enhance locking, thus decreasing the likelihood of axial slip.

Figure 22A:
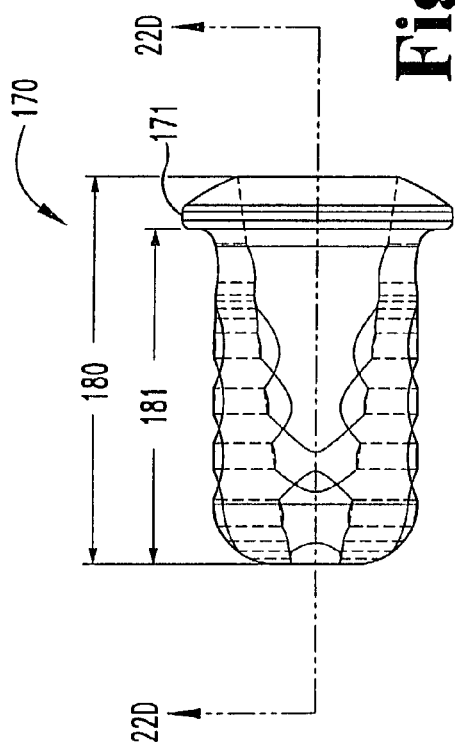
FIG. 22A is a side view of another embodiment of a shape memory tether crimp.
Figure 22C:
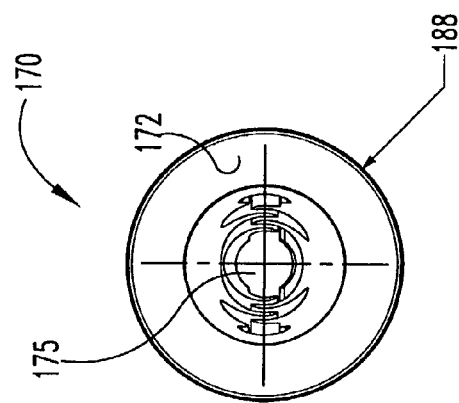
FIG. 22C is a bottom plan view of the crimp of FIG. 22A.
Figure 22B:
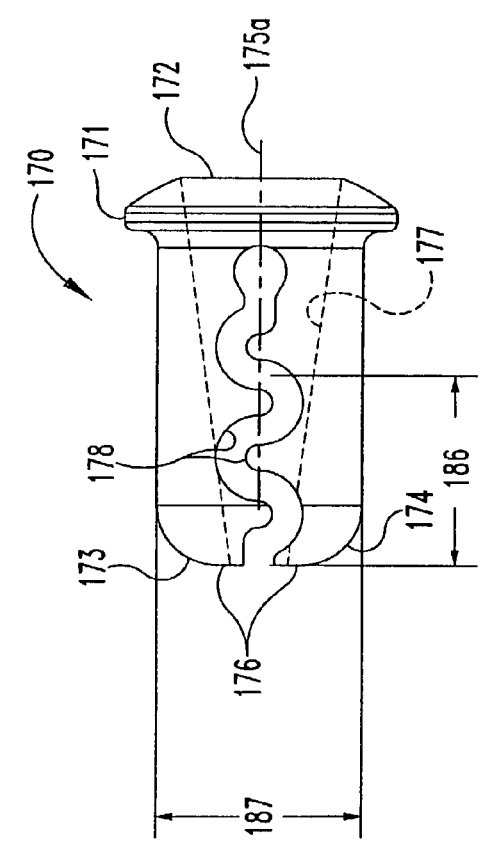
FIG. 22B is another side view of the embodiment of a shape memory tether crimp of FIG. 22A.

To better illustrate the construction of the SMA crimp 170, the dimensions of one manufactured embodiment are hereafter listed. It should be understood, however, that these dimensions are exemplary and not intended to limit the scope of protection sought. The use of dimensions and tolerances other than those listed are contemplated as within the scope of the invention. With reference to FIG. 22A, the total axial length 180 from top 176 to bottom 172 is 0.45 inches and the axial length 181 from top 172 to first portion 171 is 0.392 inches. With reference to FIG. 22B axial length 186 is 0.222 inches and the diameter 187 of the transverse cross-section of first branches 173 and 174 when at or near a closed position for SMA crimp 170 is 0.235 inches. With reference to FIG. 22C, the diameter 188 of first portion 171 is 0.3125 inches. It should be understood that cross-sections other than circular may be used.

Figure 22D:
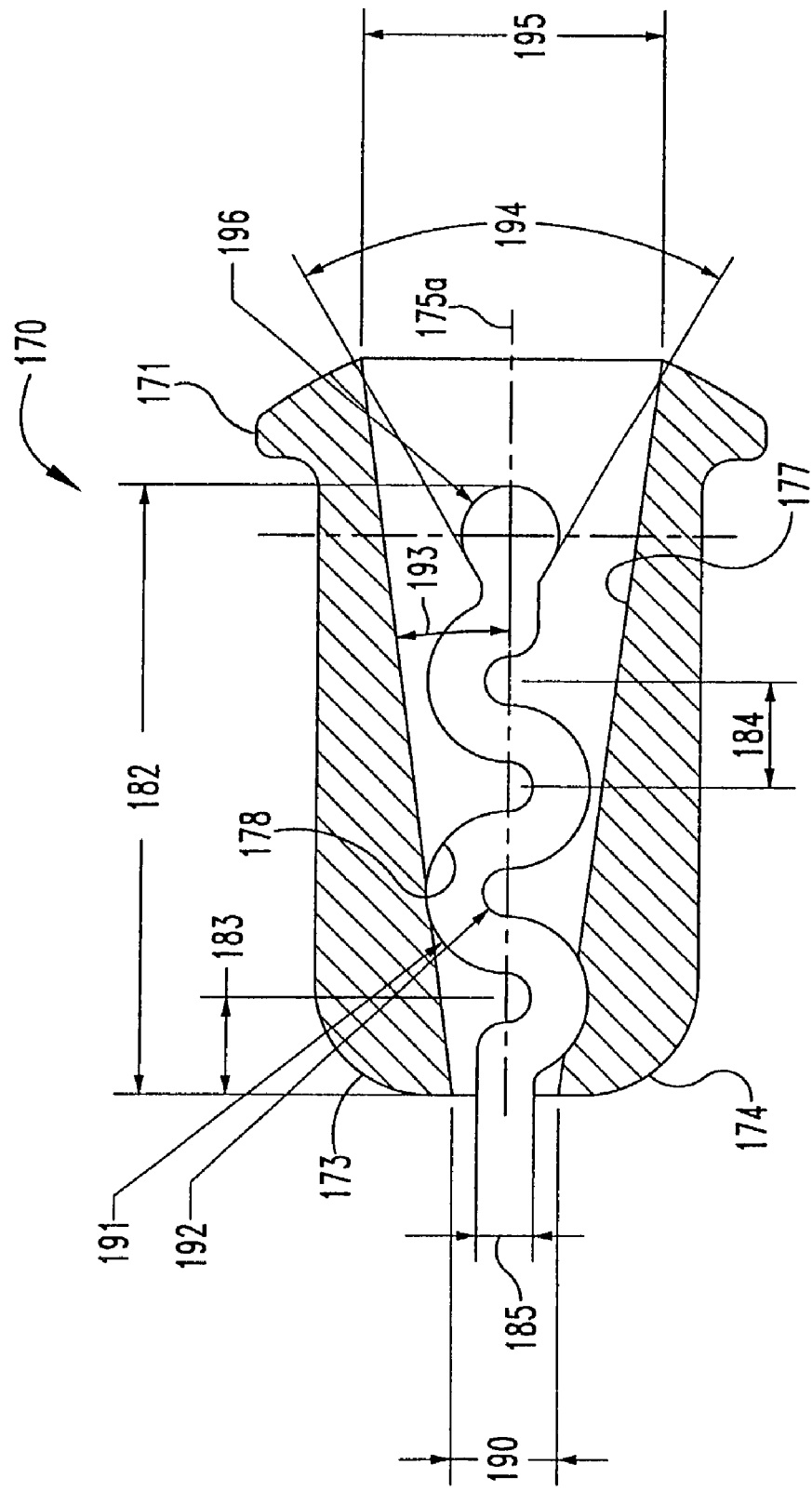
FIG. 22D is an enlarged cross-sectional view of the crimp of FIG. 22A along the direction A-A of FIG. 22A.

With reference to FIG. 22D, further dimensions are illustrated as follows: length 182 is 0.375 inches; length 183 is 0.06 inches; length 184 is typically 0.07 inches; length or diameter 185 is 0.04 inches; diameter 190 is 0.065 inches; diameter 191 is 0.10 inches; diameter 192 is 0.03 inches; angle 193 is 7.5 degrees; angle 194 is 60 degrees; and diameter 195 is 0.185 inches. As previously mentioned, variations in these design parameters that would occur to a person of ordinary skill in the art are contemplated as within the scope of the invention. It should be understood that use of the S-shaped undulations between first branch 173 and second branch 174 may be used in any of the crimps discussed previously for increased resistance to axial slip. Prior crimp designs discussed may also be similarly modified to have the first and second branches interconnected at the bottom portions as opposed to the top portion.

With reference to FIGS. 12-13, an embodiment of an adjustable spinal tether 110 is shown. Adjustable tether 110 has an artificial strand 111 with a first end 113 and a second end 115. A leader 117 has a first end 119 and a second end with a tip 121. First end 119 of leader 117 is attached to the second end 115 of strand 111. The first end 113 of artificial strand 111 may be wrapped around or otherwise attached to a grommet 123. The details of the interconnection between first end 113 and grommet 123 will be discussed further below. Grommet 123 has a top surface 125 and a bottom surface 127. Interior side surface 129 and exterior side surface 131 of grommet 123 extend between top surface 125 and bottom surface 127. The interior surface 129 defines an aperture 133 extending between top surface 125 and bottom surface 127 of grommet 123. It is understood that aperture 133 has a cross-section large enough to permit leader 117 and artificial strand 111 to be threaded therethrough in a direction from bottom surface 127 to top surface 125 or vice versa.

In one embodiment, as shown in FIGS. 12 and 13, the aperture 133 is a socket aperture sized to receive a first portion or ball portion 136 of crimp 135 therein. The crimp 135 has a barrel portion 137 protruding upward from ball portion 136 (which is preferably but not necessarily spherical). After ball portion 136 is seated in the socket aperture 133 of grommet 123 the edge 129a of aperture 133 at top surface 125 is swaged in to capture ball portion 136 in the socket aperture 133, while permitting free swiveling action such that the axis 139 of the barrel portion 137 of crimp 135 can move in a cone about the center.

The details of the construction of artificial strand 111 are identical to those discussed previously for artificial strand 11. To reiterate, one preferred embodiment is an artificial strand 111 having an inner core and outer sheath both made of polyethylene. The inner core is braided for strength while the outer sheath is braided for abrasion resistance. It should be understood that the variations and construction details previously mentioned with respect to artificial strand 11 are equally applicable to artificial strand 111. It should be further understood that many of the grommet structures described below may also be used with mechanical crimp and locknut of FIGS. 7-9.

With reference to FIGS. 12-17, it is understood that various configurations are possible for the grommet and, additionally, various interconnections between the first end 113 of artificial strand 111 and the grommet are contemplated as within the scope of the invention. For instance, (see FIGS. 12-13) grommet 123 preferably has outwardly extending flanges (130a, 130b) on exterior side surface 131 adjacent top surface 125 and bottom surface 127 respectively. These flanges aid in retention of artificial strand 111 in embodiments where artificial strand 111 is wrapped around the exterior side surface 131 of grommet 123.

In other embodiments, first end portion 113 of artificial strand 111 is wrapped around exterior side surface 131 of grommet 123 and the interconnection in which first end portion 113 is attached to artificial strand 111 may take a wide variety of configurations. In one embodiment (see FIG. 17A) first end portion 113 is adjacent artificial strand 111 and is sewn with a thread 134. Alternatively, the first end portion 113b may be attached or coupled to itself or the artificial strand 111b with a sleeve or crimp 143 (see FIG. 17B) encircling part or all of both strand 111b and first end portion 113b. In another embodiment (see FIG. 17C) the first end portion 113c contacts itself or artificial strand 111c along a contact portion or surface 135. In the embodiment as in FIG. 17C, adhesive could be applied on first end portion 113c and/or strand 111c at contact portion 135. In other possible embodiments first end portion 113b could be swaged, press fit, or even welded along contact surface 135 if strand 111c is a metal. In yet another embodiment the strand 111c is a polymer at its first end portion 113c. In this embodiment either or both of strand 111c and first end portion 113c may be ultrasonically or otherwise melted along contact surface or line 132 and then allowed to resolidify while in contact to fuse first end portion 113 to artificial stand 111c.

Additionally, in connecting first end portion 113 to grommet 123, it is not necessary to wrap first end portion 113 entirely around exterior side surface 131. For example, first end portion 113 may only partially encircle the exterior side surface 131 of grommet 123, being attached thereto with an adhesive such as epoxy. Another possibility exists when artificial strand 111, and correspondingly first end portion 113, are a multifilament polymer in which case the filaments of first end portion 113 can be separated down the middle to create an opening within first end portion 113. In yet another embodiment first end portion 113 may be wrapped around exterior side surface 131 of grommet 123 and then threaded through an opening created in first end portion 113 and knotted to secure it. In yet another embodiment there may be openings defined between exterior surface 131 and interior surface 129 of grommet 123. First end portion 113 could be threaded through some or all of these openings to attach it to grommet 123. Combinations of all the above-described mechanisms for attaching first end portion 113 to grommet 123 are contemplated as within the scope of the invention. In all cases it is preferable to give a rough finish to exterior surface 131 to increase the frictional interaction between exterior surface 131 and first end portion 113 for better gripping.

Figure 14A:
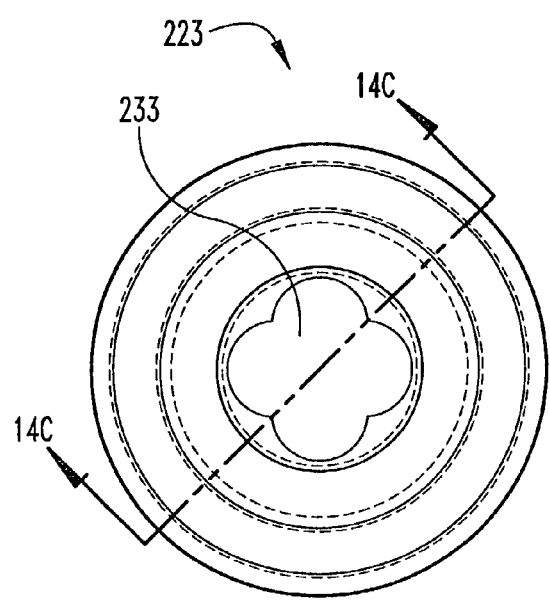
FIG. 14A is a top plan view of a self-locking grommet.
Figure 14B:
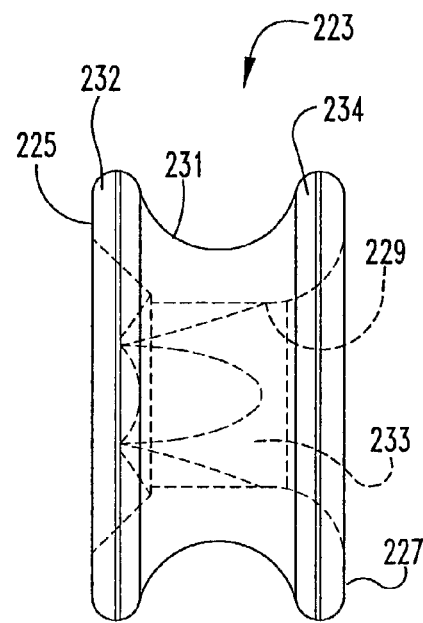
FIG. 14B is a side view of the self-locking grommet of FIG. 14A.
Figure 14C:
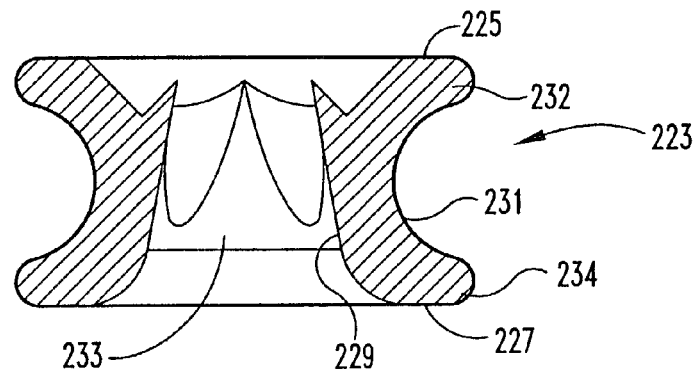
FIG. 14C is a cross-sectional view along the direction 14c of the self-locking grommet of FIG. 14A.
Figure 17A:
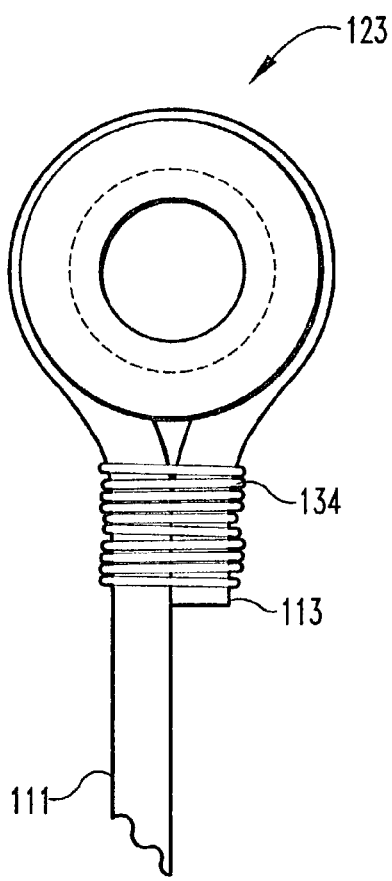
FIG. 17A is an enlarged partial view of the embodiment of the artificial strand wrapped around a grommet and attached with threading.
Figure 17B:
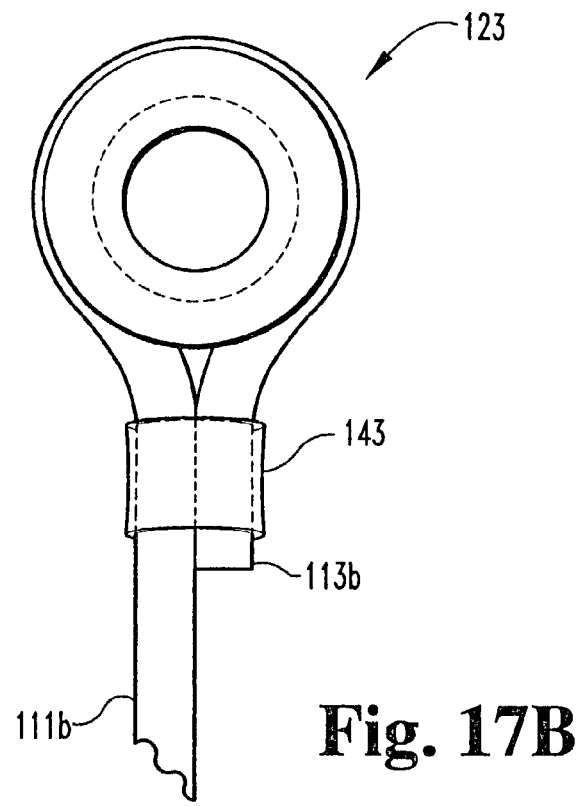
FIG. 17B is an enlarged partial view of the artificial strand wrapped around a grommet and held together with a sleeve.
Figure 17C:
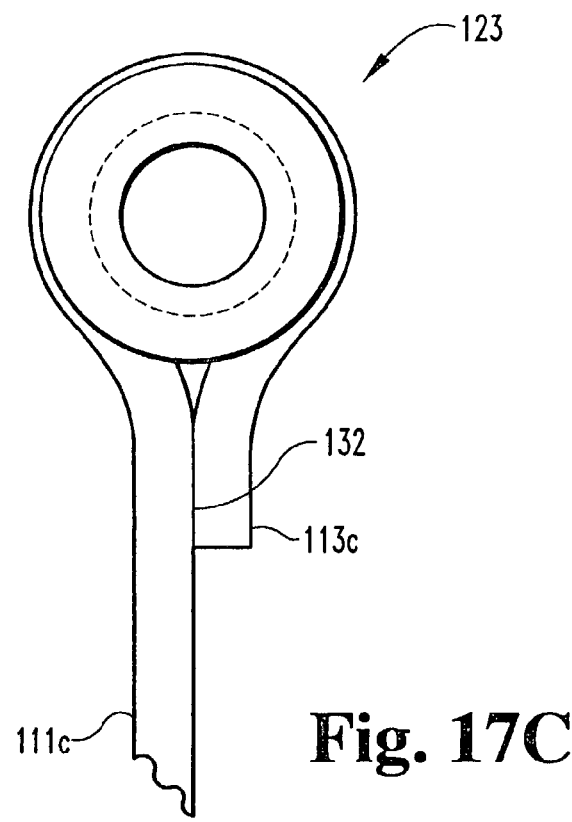
FIG. 17C is an enlarged partial view of the artificial strand attached to the grommet along a contact surface.

Further variations of grommet 123 are shown in FIGS. 14-16. FIGS. 14A-C illustrate a self-locking grommet 223 with a top surface 225 and a bottom surface 227. Interior side surface 229 and exterior side surface 231 extend between top surface 225 and bottom surface 227. Exterior side surface 231 is slanted outward adjacent top surface 225 and bottom surface 227 to create flanges 232 and 234. It should be noted that interior surface 229 defines an aperture 233 which narrows as it progresses from bottom surface 227 to top surface 225. The structure of interior surface 229 narrows in an uneven manner creating the surface mirroring the points of a crown as best shown in FIG. 14C.

In yet another embodiment (see FIGS. 15A-D) a crimping grommet 323 is provided with a barrel portion 324. The barrel portion 324 is integrally formed with crimping grommet 323 and the barrel portion 324 may be crimped inward onto an artificial strand obviating the need for a separate crimp as in some previously described embodiments. The exterior wall and flange details of the construction of crimping grommet 323 are similar to those of grommets previously described. Crimping grommet 323 has a top surface 325 and a bottom surface 327 with interior side surface 329 and exterior side surface 331 extending between top surface 325 and bottom surface 327. Interior side surface 329 defines an aperture 333 with a cross-section large enough for artificial strand 111 and leader 117 to pass therethrough. The exterior surface 331 extends outward adjacent top surface 225 and bottom surface 227 forming outwardly extending flanges 332 and 334. The cross-section of aperture 333 narrows slightly from bottom flange 334 moving toward top surface 325 and barrel portion 324. After aperture 333 narrows slightly it then has a constant cross-section which extends through the remainder of grommet 323 as well as barrel portion 324. It should be understood, however, that various cross-sections are contemplated as within the scope of the invention.

An alternative embodiment, crimping grommet 323a is shown in FIGS. 16A-D where like elements are labeled as previously. Instead of having a barrel portion 324, crimping grommet 323a has a plurality of prongs 324a extending upward from the top surface 325 of grommet 323a. These prongs 324a may be bent inwardly to compress upon an artificial strand 111 extending through the aperture 333 defined by interior surface 329 of crimping grommet 323a.

All embodiments of the grommet are preferably made of titanium alloy (ASTM F138). It should be understood, however, that various biocompatible materials are contemplated for use in manufacturing the embodiments of the grommet described above. Conventional implant alloys such as stainless steel, cobalt-chrome alloys and even shape memory alloys may be used to manufacture the grommet. For example, barrel portion 324 or prongs 324a may be made of shape memory material which, when heated (or upon the release of stress if stressed to permit an artificial strand to pass through), will reform to its memorized shape which compresses inward on the artificial strand 111 passing through aperture 333. The inward compression will prevent or minimize motion of artificial strand 111 relative to the grommet.

Alternatively the grommet may be manufactured from various polymers. It should be understood, however, that the friction between the exterior side surface of the grommet and the first end portion of the artificial strand may be reduced below an acceptable level if both the grommet and the artificial strand are manufactured from a polymer such as ultra high molecular weight polyethylene. It is preferable to make the grommet from an alloy and provide a rough surface finish to the exterior side surface to increase the frictional engagement between the grommet and the artificial strand. The aperture defined within the grommet may take a variety of cross-sections including, but not limited to a circular ring, oval, elliptical, triangular, square, other polygons, and other cross-sections exterior or interior.

Figure 18B:
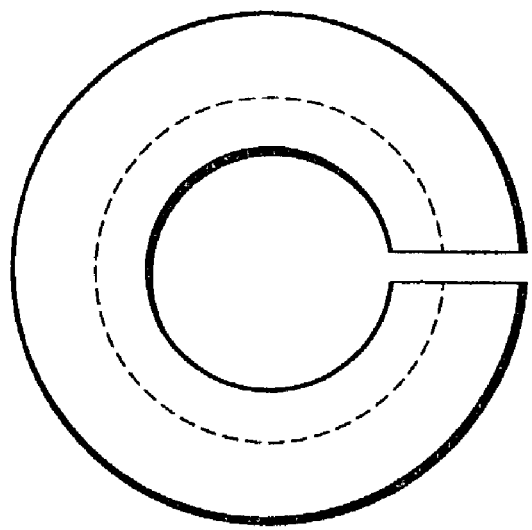
FIG. 18B is an illustration of a grommet of the present invention which is an open ring.
Figure 18A:
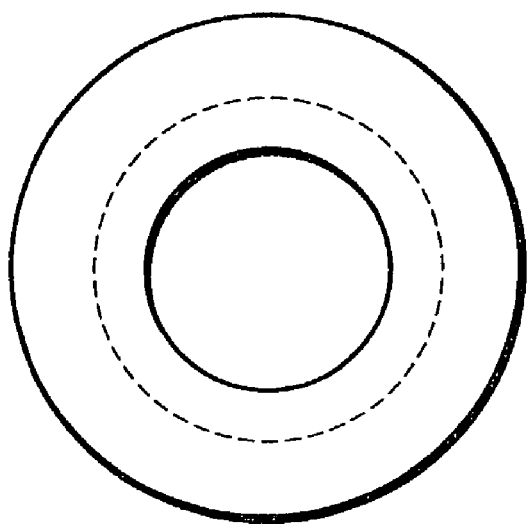
FIG. 18A is an illustration of a grommet which is a closed ring.

Additionally, it may be preferable to provide the aperture defined by the interior side surface of the grommet with a coating to minimize the stress on the artificial strand within the aperture portion of the grommet. It should be understood that in all of the above embodiments the term "grommet" encompasses both a closed ring structure as shown in FIG. 18A or an open ring structure as illustrated in FIG. 18B, wherein the grommet has a C-shaped structure extending between its top surface and its bottom surface. Also, as suggested above, it may be of a shape other than the circular shape shown in FIGS. 18A and 18B. Additionally, it should be further understood that the attachment of the first end portion of the artificial strand to any of the grommets may be done in various manners as previously described in relation to first end portion 113 and grommet 123.

With reference to FIG. 19, a plug and ring design 400 for securing an adjustable length of artificial strand 411 is shown. The plug and ring design 400 comprises a ring 429 with an exterior side wall 430 and an interior side wall 431. Interior side wall 431 defines an aperture 433 through the ring. In operation, one end of artificial strand 411 extends through the aperture 433. As discussed in previous embodiments, the artificial strand 411 may consist of an outer sheath and an inner core. The outer sheath is stripped back and a plug 435 is inserted into aperture 433 to squeeze the circular fibers of the stronger inner cord of artificial strand 411 which have been separated as shown into branches 415*a* and 415*b*. It should be understood that, as opposed to two branches 415*a* and 415*b*, plug 435 may contact inner cord of artificial strand 411 in the form of an annular surface as opposed to the two branches 415*a* and 415*b* shown.

With reference to FIGS. 20A and 20B, the use of cams 520 to tension the cord or tether 511 is shown. The tether 511 is shown as having factory loops 512 and 513 at each end. Cams 520 are mounted at each vertebral level to tension the cord and rotate it. The cams 520 may be mounted on vertebral screws by twisting them over the bone screws 515 which can also aid in preventing screw back out. It should be understood that, as opposed to bone screws 515, the cams 520 may instead be mounted on vertebral screw-blocks to tension the cord. It should be further understood that, as opposed to factory loops 512 and 513 at each end, the cord 511 may instead be an adjustable spinal tether as in embodiments previously disclosed in this application which may or may not contain a grommet but is generally of an adjustable length. It should also be understood that while the cord 511 in FIGS. 19A and 19B is shown looped around both sides of cams 520, it may instead merely be looped around only one side of each cam 520. The cams 520 shown in FIGS. 20A and 20B are intended to be turned 90 degrees to tension the cords. Furthermore, it should be clear that the cams 520 in FIGS. 20A and 20B have already been rotated to the tensioning position.

Figures 21A, 21B:
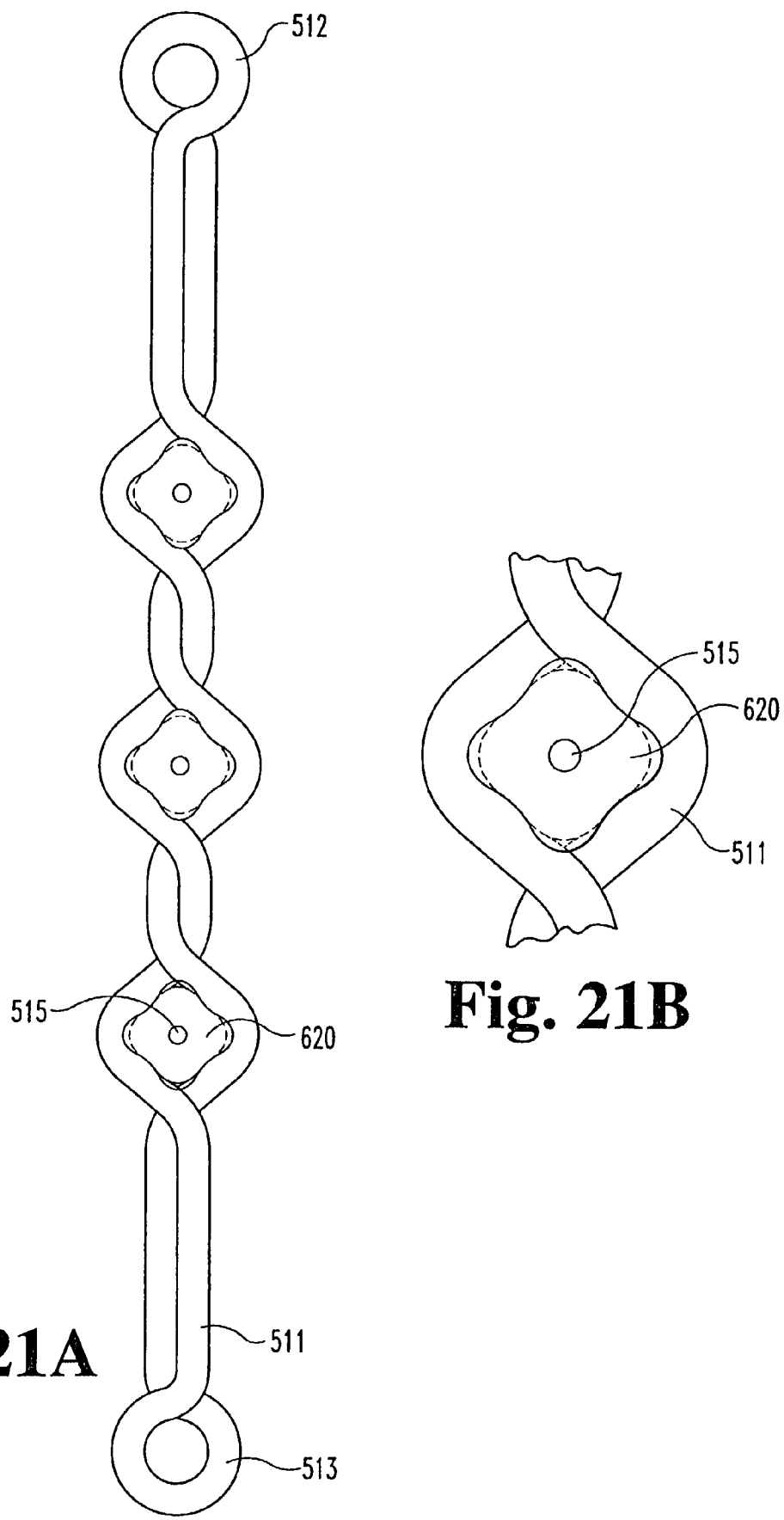
FIGS. 21A and 21B are another embodiment of cam tensioners having a shape other than oval.

With reference to FIGS. 21A and 21B, an alternative embodiment of the cams is shown in which the cam 620 has a cross-sectional shape other than the oval of FIGS. 20A and 20B. Like elements in FIGS. 21A and 21B are labeled as those in FIGS. 20A and 20B. The cam 620 in FIGS. 21A and 21B are intended to be turned in 45 degree increments to tension the cord 511 as opposed to the 90 degree rotation necessary to tension the cord with the oval shapes of cams 520. It should also be understood that other cam cross-sectional shapes other than the oval and smooth cornered square shapes of FIGS. 20-21 are possible including polygons and others known to those of ordinary skill in the art.

The various embodiments of the adjustable spinal tether may find a wide range of applications including outside of the spine. This adjustable spinal tether is intended for use in a spine for support of instabilities, correction of deformities, and as a tension band to facilitate fusion of adjacent vertebrae. In all of the aforementioned cases, the adjustable spinal tether can be used with or without spinal implants for fixation to the spinal column. One preferred application of the adjustable spinal tether is use in correction of spinal deformities through vertebral body tethering without fusion as disclosed in provisional application Ser. No. 60/130,909, filed Apr. 23, 1999, assigned to the assignee of the present application entitled "Device and Method for the Correction of Spinal Deformities Through Vertebral Body Tethering Without Fusion" and the disclosure of which is incorporated herein by reference.

The various embodiments of the adjustable spinal tether do not require any additional pieces or knots to secure itself to the spine. The adjustable spinal tether may be packaged as a complete assembly and will not require any additional components and is essentially "one size fits all." The embodiments containing a grommet are also advantageous since they do not require strand-to-strand contact stress as in the embodiments without a grommet where the strand passes through a small loop formed on one end of the strand. For purposes of this application, "strand" includes both a monofilament or single fiber as well as a multifilament or multifiber length of material.

In all cases the adjustable spinal tether may be used as follows: the leader can be used to introduce the artificial strand around or through spinal anatomy or spinal implants and back through the aperture in either the grommet or a loop in the strand and then through a crimp (or a crimping grommet as the case may be) to form a loop. With the loop completed, the adjustable spinal tether can then be tightened with a tensioner instrument such as that disclosed in U.S. Pat. No. 5,395,374 to Miller et al., the disclosure of which is incorporated herein by reference. After the tether is tightened with a tensioner instrument and then crimped, the excess artificial strand can be trimmed flush with the crimp or the crimp portion of the grommet as the case may be.

While the invention has been illustrated and described in detail in the drawings and foregoing description, the same is to be considered illustrative and not restrictive in character, it being understood that only the preferred embodiments have been shown and described and that all changes and modifications that come within the spirit of the invention are desired to be protected.

What is claimed is:

1. An adjustable tether, comprising:
   a strand having a first end portion and a second end portion, said first end portion of said strand including a first part and a second part, said first part of said strand overlapping said second part of said strand and secured thereto in wrapped condition to form a looped portion defining an aperture, said second end portion extending through said aperture to form a loop having an adjustable length; and a crimp having a passage defined therethrough, said crimp being transitionable between a first state and a second state, said first state permitting said second end portion to pass through said passage, said second state preventing said second end portion from passing through said passage, a portion of said crimp being configured to prevent said crimp from passing through said aperture; and wherein said crimp is non-axially coupled to said looped portion of said strand defining said aperture and is free to slide in an axial direction along said second end portion of said strand toward and away from said aperture when in said first state, said crimp being slidably positioned adjacent said aperture and transitioned to said second state to fix said length of said loop.

2. The adjustable tether of claim 1, wherein a second portion of said crimp is received within said aperture.

3. The adjustable tether of claim 1, wherein said strand is formed of a polymer.

4. An adjustable tether, comprising:

a strand having a first end portion and a second end portion, said first end portion of said strand secured in wrapped condition to farm an eyelet defining an aperture, said second end portion extending through aperture to form a loop having an adjustable length; and a crimp having a passage defined therethrough, said crimp being transitionable between a first state and a second state, said first state permitting said second end portion to pass through said passage, said second state preventing said second end portion from passing through said passage, a portion of said crimp being configured to prevent said crimp from passing through said aperture; and wherein said crimp is non-axially counled to said looped portion of said strand defining said aperture and is free to slide in an axial direction along said second end portion of said strand toward and away from said aperture when in said first state, said crimp being slidably positioned adjacent said aperture and transitioned to said second state to fix said length of said loop.

5. The adjustable tether of claim 4, wherein said first end portion includes a first part and a second part; and wherein said first part is attached to said second part by an epoxy to form said eyelet.

6. The adjustable tether of claim 4, wherein said first end portion includes a first part and a second part; and wherein said first part is attached to said second part by a thread sewn around said first and second parts to form said eyelet.

7. The adjustable tether of claim 4, wherein said strand is formed of a polymeric material.

8. An adjustable tether, comprising:

a strand formed of a polymeric material and having a first end portion and a second end portion, said first end portion of said strand secured in wrapped condition to form an eyelet defining an aperture, said first end portion including a first part and a second part, said first part being attached to said second part by melting at least a portion of each of said first and second parts and fusing the melted portions together to form a solidified polymer, said second end portion extending through said aperture to form a loop; and a crimp having a passage defined therethrough, said crimp being transitionable between a first state and a second state, said first state permitting said second end portion to pass through said passage, said second state preventing said second end portion from passing through said passage, a portion of said crimp being configured to prevent said crimp from passing through said aperture.

9. An adjustable tether, comprising:

a strand having a first end portion and a second end portion; and a grommet, said first end portion of said strand operatively attached to said grommet with said grommet defining an aperture, said second end portion of said strand extending through said aperture to form a loop having an adjustable length; and a crimp having a passage defined therethrough, said crimp being transitionable between a first state and a second state, said first state permitting said second end portion to pass through said passage, said second state preventing said second end portion from passing through said passage, a portion of said crimp being configured to prevent said crimp from passing through said aperture; and said crimp being variably positionable relative to said grommet, said crimp cooperating with said grommet to fix said length of said loop when transitioned to said second state.

10. The adjustable tether of claim 9, wherein said first end portion of said strand includes a first part and a second part, said first part being wrapped about an exterior surface of said grommet and operatively secured to said second part.

11. The adjustable tether of claim 9, wherein said strand is formed of a polymer.

12. The adjustable tether of claim 9, wherein said strand is formed of a polymer;

13. The adjustable tether of claim 12, wherein said first end portion includes a first part and a second part, said first part being wrapped about an exterior surface of said grommet and operatively secured to said second part.

14. The adjustable tether of claim 13, wherein said first part is attached to said second part by an epoxy.

15. The adjustable tether of claim 13, wherein said first part is attached to said second part by a thread sewn around said first and second parts.

16. The adjustable tether of claim 13, wherein said first part is attached to said second part by melting at least a portion of each of said first and second parts and fusing the melted portions together to form a solidified polymer.

17. The adjustable tether of claim 12, wherein said polymer strand has an inner core and a braided outer sheath.

* * * * *